(12) United States Patent
Sano et al.

(10) Patent No.: US 11,154,856 B2
(45) Date of Patent: Oct. 26, 2021

(54) TEST DEVICE

(71) Applicant: KANEKA CORPORATION, Osaka (JP)

(72) Inventors: Sotaro Sano, Hyogo (JP); Shigehiko Miyamoto, Hyogo (JP); Takaaki Jikihara, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 331 days.

(21) Appl. No.: 16/259,277

(22) Filed: Jan. 28, 2019

(65) Prior Publication Data

US 2019/0168209 A1    Jun. 6, 2019

Related U.S. Application Data

(63) Continuation of application No. PCT/JP2017/026637, filed on Jul. 24, 2017.

(30) Foreign Application Priority Data

Jul. 29, 2016  (JP) .............................. JP2016-150452

(51) Int. Cl.
*B01L 3/00* (2006.01)
*G01N 30/91* (2006.01)
(Continued)

(52) U.S. Cl.
CPC .............. *B01L 3/502* (2013.01); *C12M 1/00* (2013.01); *C12Q 1/6844* (2013.01); *G01N 30/90* (2013.01); *G01N 30/91* (2013.01); *G01N 30/92* (2013.01)

(58) Field of Classification Search
CPC ......... B01L 2200/022; B01L 2200/025; B01L 2200/026; B01L 2200/0642;
(Continued)

(56) References Cited

U.S. PATENT DOCUMENTS

2002/0085958 A1   7/2002   Nemcek et al.
2007/0122848 A1   5/2007   Mizutani
(Continued)

FOREIGN PATENT DOCUMENTS

JP   2003-500651 A   1/2003
JP   2007-178423 A   7/2007
(Continued)

OTHER PUBLICATIONS

International Search Report issued in International Application No. PCT/JP2017/026637, dated Oct. 3, 2017 (5 pages).
(Continued)

*Primary Examiner* — Jennifer Wecker
*Assistant Examiner* — Jonathan Bortoli
(74) *Attorney, Agent, or Firm* — Osha Bergman Watanabe & Burton LLP

(57) ABSTRACT

A test device includes a housing and a lid. The housing encloses an internal space, has a hole supporting a container accommodating liquid, and includes a perforation/incision part. The lid covers a hole-formed part of the housing. The housing and/or the lid includes a guide that guides the housing and the lid, so that the lid can migrate from the first position to the second position while covering the hole-formed part of the housing. In the first position, the lid covers the hole-formed part of the housing and the container and the container is not incised. During the migration of the lid from the first position to the second position, the container is pushed toward the perforation/incision part by the lid, and the container is incised to leak liquid into the internal space.

6 Claims, 26 Drawing Sheets

(51) Int. Cl.
*G01N 30/92* (2006.01)
*G01N 30/90* (2006.01)
*C12M 1/00* (2006.01)
*C12Q 1/6844* (2018.01)

(58) Field of Classification Search
CPC ......... B01L 2300/042; B01L 2300/044; B01L 2300/0672; B01L 2300/0858; B01L 3/502; B01L 3/5023; B01L 3/5025; B01L 3/502715; C12M 1/00; C12Q 1/6844; G01N 30/90; G01N 30/91; G01N 30/92
See application file for complete search history.

(56) References Cited

U.S. PATENT DOCUMENTS

| | | | | |
|---|---|---|---|---|
| 2008/0124244 | A1* | 5/2008 | Sigel | G01N 33/558 422/400 |
| 2009/0181388 | A1* | 7/2009 | Qimin et al. | C12Q 1/68 435/6 |
| 2010/0285454 | A1 | 11/2010 | You et al. | |
| 2011/0181875 | A1* | 7/2011 | Nakahana | B01L 3/5453 356/246 |
| 2015/0050720 | A1 | 2/2015 | Montero et al. | |
| 2015/0203904 | A1 | 7/2015 | Hopper | |
| 2017/0153232 | A1 | 6/2017 | Zhu | |

FOREIGN PATENT DOCUMENTS

| | | |
|---|---|---|
| JP | 2010-500009 A | 1/2010 |
| JP | 2015-512250 A | 4/2015 |
| WO | 2016061810 A1 | 4/2016 |

OTHER PUBLICATIONS

Written Opinion issued in International Application No. PCT/JP2017/026637, dated Oct. 3, 2017 (8 pages).

Supplementary Partial European Search Report issued in corresponding European Application No. 17834225.9; dated Jan. 16, 2020 (14 pages).

* cited by examiner

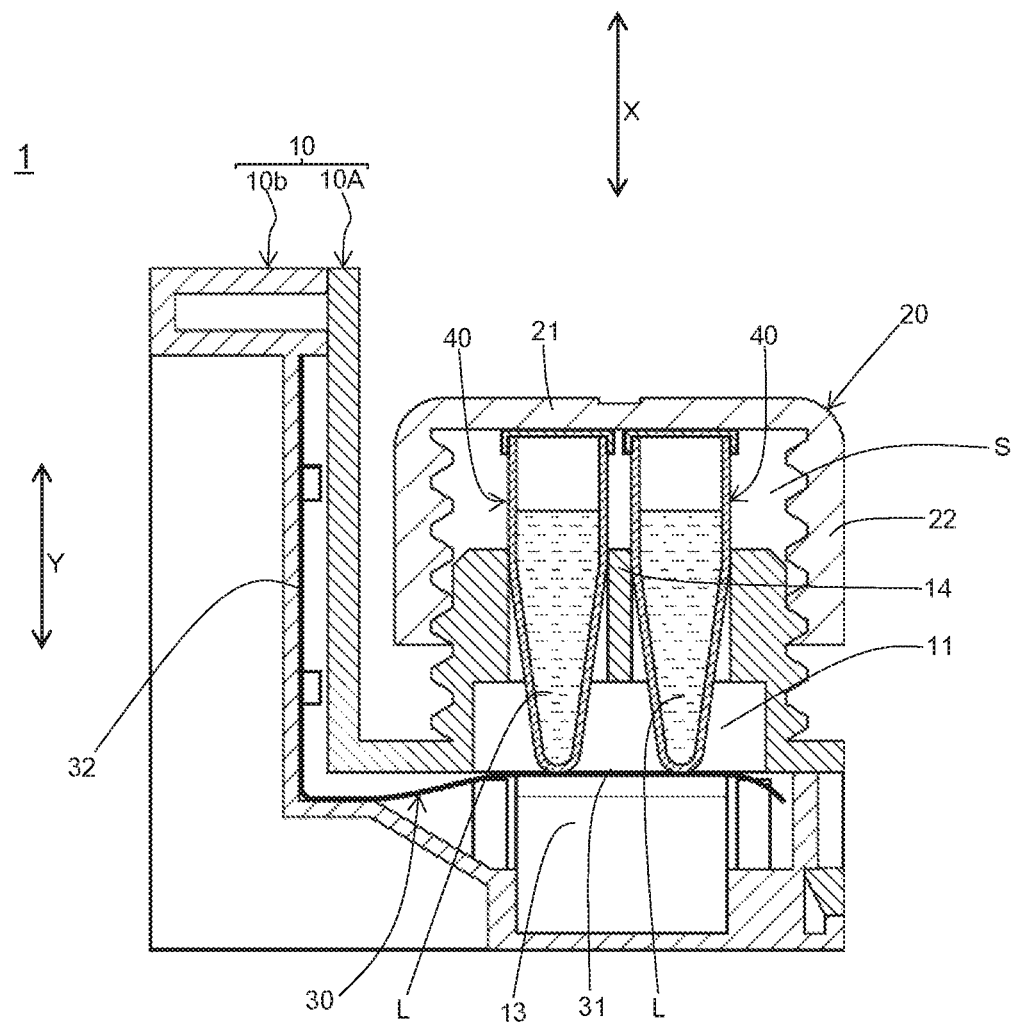

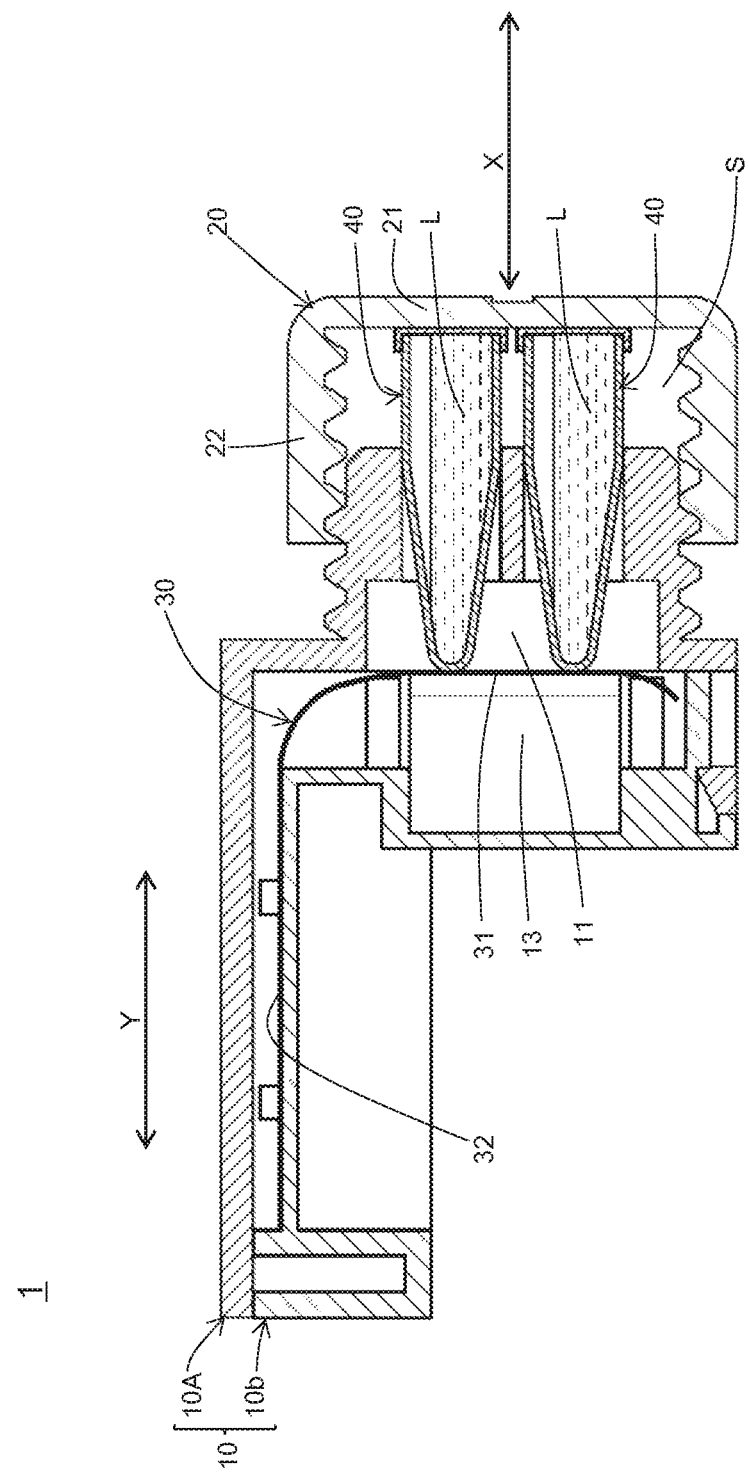

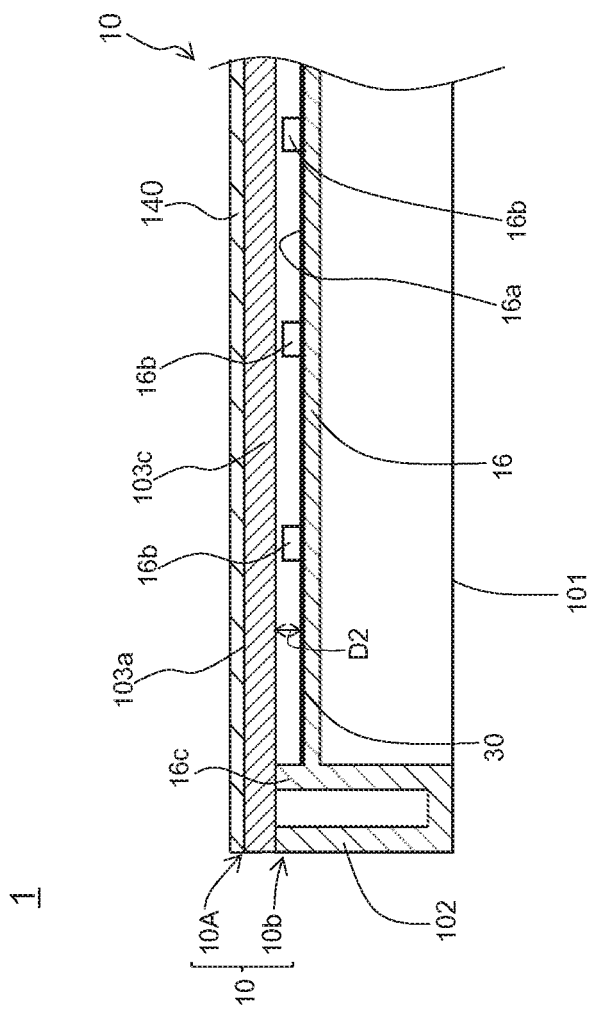

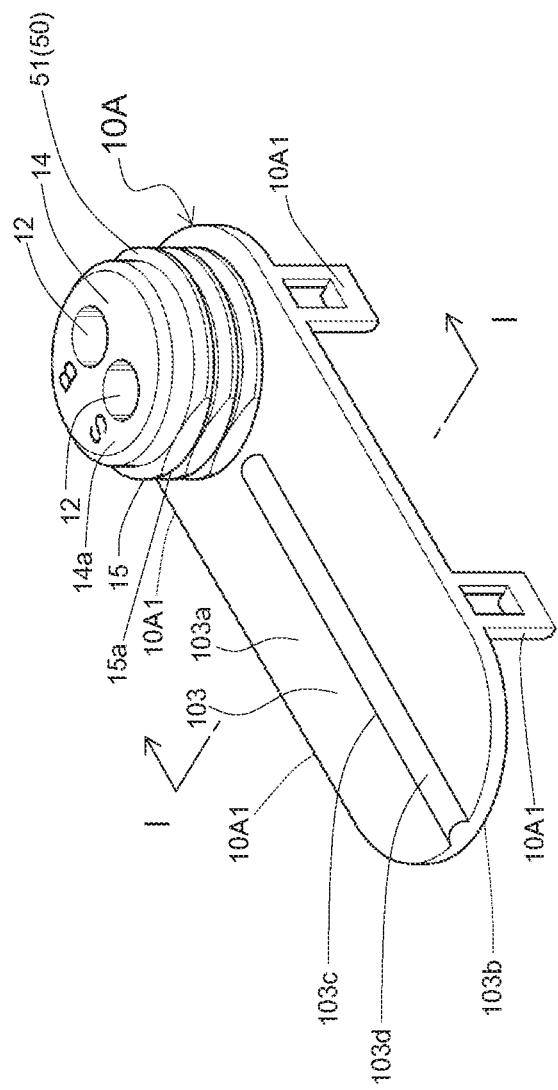

TEST DEVICE

TECHNICAL FIELD

One or more embodiments of the present invention relate to a test device used fix chromatography.

BACKGROUND

Nucleic acid chromatography is carried out on a chromatography support comprising a nucleic acid immobilized thereon to develop, capture, and detect a detection target comprising a nucleic acid tag hybridizing to the nucleic acid immobilized on the support. Nucleic acids comprising different nucleotide sequences are immobilized on a chromatography support at different positions, and each of a plurality of detection targets is tagged with a nucleic acid tag specific to the nucleic acid, so that a plurality of detection targets contained in a single specimen can be detected on a single support. In addition to nucleic acid chromatography, techniques of chromatography comprising capturing the detection targets on a chromatography support with the use of an antigen-antibody combination or a ligand-receptor combination capable of forming a specific bond are extensively used in the field of, for example, molecular biological testing or genetic testing for medical or food testing.

The chromatography techniques as described above involve the use of various types of liquids, such as a sample liquid containing detection targets or developing liquids. When such liquids are removed from a container with the use of an instrument, such as a pipette, and applied to a chromatography support, the liquid may disperse in the testing environment and contaminate the environment, which may lead to a false-positive result. By opening the container in the test environment, a liquid in the container may be contaminated.

An apparatus that breaks a part of a container to allow a liquid to leak therefrom and brings the leaked liquid into contact with a chromatography support while maintaining a liquid, such as a sample liquid or developing liquid, used for chromatography inside the container without the use of an instrument, such as a pipette, has been developed.

For example, a device for detection of analytes in affinity bioassays disclosed in Patent Document 1 comprises at least one transparent wall, at least one test recess adapted to receive at least one test strip and arranged in a manner such that said test strip is visible through the transparent wall, at least one cavity adapted to receive a container accommodating a fluid sample, said cavity being in fluid communication with said at least one test recess, and piercing means arranged in correspondence with said at least one cavity, in a manner such that, upon insertion of a container in the cavity, the container is pierced and at least an area of the sample is released from the container and reaches the test recess.

Also, a totally-enclosed device for quick detection of a target nucleic acid amplification product disclosed in Patent Document 2 comprises an inner core and an outer casing, wherein the inner core comprises a fixing case part and a base part, the fixing case part being provided with two holes respectively for housing washing buffer vacuoles and a PCR tube containing an amplification product, the base part comprising a washing buffer container element having a vacuole puncture needle, an amplification product container element having a blade, a sealing diaphragm, a piece of glass fiber paper, and a test strip sealing part having a transparent window; and the outer casing comprises a handle cover, a fixing case pressing part, a washing buffer vacuole extruding part, and a transparent window.

Patent Document 1: JP 2015-512250 A
Patent Document 2: JP 2010-500009 A

Patent Document 1 discloses that a container accommodating a liquid containing a sample is pierced only when the container is inside the device and the container is then released on a test strip. Thus, sample contamination can be avoided.

In Patent Document 1, however, contamination may not be sufficiently prevented. In the device according to Patent Document 1, the opening of the recess into which the container is to be inserted is open to the outside. When the container is inserted into and pushed down in the recess and the liquid is released by piercing the container, accordingly, a liquid may leak from the space between the container and the recess. When the container is pierced by a piercing means, the pressure inside the container may be elevated upon invasion of the piercing means into the bottom of the container, and an opening at the top of the container may open.

Patent Document 2 also discloses that use of the device disclosed in Patent Document 2 enables testing of a PCR amplified product in a totally enclosed state and prevention of an experimental laboratory from contamination.

However, the structure of the device according to Patent Document 2 is complicated. This complicates the operation and increases a risk of errors. Thus, such device is not preferable. In addition, contamination may not be sufficiently prevented with the use of the device according to Patent Document 2. In the device according to Patent Document 2, a fixing case part is composed of two members comprising a hole corresponding to a PCR tube when they are superposed to each other, and the two members laterally sandwich the PCR tube in positions in the vicinity of the opening at the top of the PCR tube to fix the PCR tube. When sandwiching a PCR tube with the two members, it is necessary to arrange the PCR tube in adequate directions. When the PCR tube is not adequately arranged, the opening of the PCR tube may be opened, disadvantageously.

SUMMARY

One or more embodiments of the present invention provide a test device that can reduce contamination when a liquid comes into contact with a chromatography support.

One or more embodiments of the present invention provide a test device that is provided with a simple mechanism for allowing a liquid used for chromatography to efficiently leak from the container accommodating the liquid.

One or more embodiments of the present invention provide a test device that is provided with a chromatography support accommodated in a housing and is easily observed from the outside of the housing.

One or more embodiments of the present invention provide a test device comprising a chromatography support accommodated in a housing that can allow a liquid used for chromatography to leak from the container accommodating the liquid and efficiently bring the liquid into contact with the support.

The test device according to one or more embodiments of the present invention comprises:

a housing enclosing an internal space where chromatography involving the use of a chromatography support is carried out, the housing having at least one hole through which the internal space is communicated with the outside and at least one container accommodating a liquid used for chromatography is inserted and supported, and the housing comprising a perforation/incision part provided in the internal space that perforates or incises the container to leak the liquid from the container into the internal space; and a lid mounted on the housing that covers a hole-formed part of the housing where the at least one hole is formed, wherein at least either one of the housing and the lid comprises a guide that guides the lid to the housing in a manner such that, while the lid covers the hole-formed part of the housing, the lid can migrate from a first position where the lid covers the hole-formed part of the housing while keeping a space therebetween and where the distance between the hole-formed part of the housing and a part of the lid facing the hole-formed part of the housing designated as a first distance to a second position where the lid covers the hole-formed part of the housing and where the distance between the hole-formed part of the housing and a part of the lid facing the hole-formed part of the housing is a second distance smaller than the first distance, when the lid is allowed to migrate from the first position to the second position while supporting the container through the at least one hole of the housing and covering the hole-formed part of the housing with the lid, the first position is a position where the lid covers the hole-formed part of the housing and an outer portion of the container protruded toward the lid through the at least one hole and the container is not perforated or incised at the perforation/incision part, and while the lid is allowed to migrate from the first position to the second position, the housing and the lid are guided by the guide in a manner such that the part of the lid abuts against an end of the outer portion of the container, the container is pushed toward the perforation/incision part, and the perforation/incision part perforates or incises the container to leak the liquid into the internal space.

With the use of the test device according to one or more embodiments of the present invention, for example, a risk of contamination occurring when a liquid comes into contact with the chromatography support is reduced by the action described below.

At the outset, the container accommodating a liquid is inserted into and supported by the at least one hole of the housing and the lid is positioned in the first position with respect to the housing. In such a state, the lid covers the hole-formed part of the housing and the outer portion of the container protruding from the at least one hole toward the lid. However, the perforation/incision part does not perforate or incise the container in that state. Specifically, the outer portion of the container and the hole-formed part of the housing are covered by the lids before liquid leaks from the container.

Subsequently, during the process of migration of the lid from the first position to the second position, the part of the lid abuts against the end of the outer portion of the container. Thus, the container is pushed toward the perforation/incision part, the container is perforated or incised at the perforation/incision part, and the liquid leaks into the internal space. During the process, the lid migrates while covering the hole-formed part of the housing. Thus, dispersion of a liquid leaked from the container to the outside of the test device can be suppressed. During this process, in addition, the part of the lid abuts against the end of the outer portion of the container. When a microtube comprising an opening at the end is used as the container, the opening of the microtube would not be opened unintentionally.

According to one or more embodiments of the test device of the present invention, the housing comprises a lid-mounting part formed to surround the hole-formed part of the housing on which the lid is to be mounted, and when the housing with the container inserted into and supported by the at least one hole of the housing is viewed from the outside of the housing in the through-hole direction, the housing is constructed in a manner such that a profile of the outer portion of the container is enclosed within the inner periphery of the lid-mounting part.

According to one or more embodiments of the test device of the present invention, the lid can be easily mounted while the container is inserted into and supported by the at least one hole of the housing, and migration of the lid from the first position to the second position is less likely to be blocked by the outer portion of the container.

According to one or more embodiments of the test device of the present invention, the guide comprises a power boost mechanism that allows the lid mounted on the housing to migrate from the first position to the second position.

According to one or more embodiments of the test device of the present invention, the lid mounted on the housing can easily migrate from the first position to the second position.

According to one or more embodiments of the test device of the present invention, the guide comprises screw-engagement parts formed on the lid and the housing, and the screw-engagement parts are engaged with each other in a manner such that, when the lid mounted on the housing in the first position is revolved around the axis along the direction in which the hole-formed part of the housing faces the lid, the lid migrates along the axis toward the hole-formed part of the housing.

According to one or more embodiments, a power of allowing the lid to revolve is utilized, so that the lid mounted on the housing can migrate from the first position to the second position. While the lid migrates from the first position to the second position, the lid revolves in a manner such that the inner surface of the lid abuts against the end of the outer portion of the container. As a result, friction occurs, and torsion is applied to the container in a direction approximately vertical to the axis. This accelerates the liquid to leak from the container.

According to one or more embodiments of the test device of the present invention, the housing comprises, in a position surrounding the at least one hole, an elastic member that urges the container supported by the at least one hole against the axis of the hole and retains the position of the container within the hole.

According to one or more embodiments of the test device of the present invention, the position of the container inserted into the hole is retained by the elastic member. Thus, the position of the container relative to the perforation/incision part can be stabilized.

According to one or more embodiments of the test device of the present invention, a concave-convex surface, such as an undulated surface, is provided on the lateral surface of the housing.

According to one or more embodiments of the test device of the present invention, slip caused when a user operates the test device with fingers can be prevented. When a plurality of test devices are arranged in such a manner that lateral surfaces face each other, a concave surface can be engaged with a convex surface.

The test device according to one or more embodiments of the present invention comprises:

a housing for accommodating a chromatography support, the housing enclosing an internal space where chromatography involving the use of the chromatography support is carried out, wherein the housing comprises a supporting part for supporting two or more containers accommodating liquids used for chromatography, and a perforation/incision part that perforates or incises by itself the two or more containers supported by the supporting part to leak the liquids from the containers into the internal space.

With the use of the test device according to one or more embodiments of the present invention, two or more containers can be perforated or incised at the one perforation/incision part to leak the liquids from the containers. Thus, the mechanism can be simplified, and production cost can be reduced.

The test device according to one or more embodiments of the present invention comprises:

a chromatography support; and a housing accommodating the chromatography support, the housing enclosing an internal space where chromatography involving the use of the chromatography support is carried out, wherein the housing comprises:

a bottom wall;

an upper wall facing the bottom wall;

a side wall connecting the periphery of the bottom wall to the periphery of the upper wall; and a support-mounting part for providing the support in a direction facing the upper wall in a position closer to the upper wall between the bottom wall and the upper wall in the direction in which the bottom wall faces the upper wall, the support is provided on the support-mounting part of the housing, and a part of the upper wall facing the support is visible light permeable.

In the test device according to one or more embodiments of the present invention, a chromatography support is disposed in a position close to the upper wall of the housing, and the upper wall is visible light permeable. Thus, the support is sufficiently visible at the time of chromatographic development.

In the test device according to one or more embodiments of the present invention, preferably, the distance between the part of the support provided on the support-mounting part and the upper wall is 10 mm or less. According to one or more embodiments, the support is more sufficiently visible from the outside of the housing through the upper wall.

In the test device according to one or more embodiments of the present invention, preferably, a surface facing the upper wall of the support is covered by a visible light permeable protective film. According to one or more embodiments, the support is more sufficiently visible from the outside of the housing through the upper wall.

In the test device according to one or more embodiments of the present invention, preferably, the part of the upper wall facing the support has a thickness of 20 μm to 10 mm and total luminous transmittance of 70% or more. According to one or more embodiments, the support is more sufficiently visible from the outside of the housing through the upper wall.

In the test device according to one or more embodiments of the present invention, in the plane view of the housing, an area accounting for 5% or more of the total area of the housing is preferably a visible light permeable part of the upper wall facing the support. According to one or more embodiments, the support is more sufficiently visible from the outside of the housing through the upper wall.

In the test device according to one or more embodiments of the present invention, preferably, at least either one of the outer surface and the inner surface of the upper wall is provided with an anti reflection member. According to one or more embodiments, the support is more sufficiently visible from the outside of the housing through the upper wall.

The test device according to one or more embodiments of the present invention preferably comprises a visible light permeable protrusive part extending along the support toward the outside of the housing in a position outside of the housing in a part of the upper wall facing the support. According to one or more embodiments, when the support is observed under a visible light through the protrusive part of the upper wall, an image of the support is enlarged by the protrusive part. Thus, visibility of the support can further be enhanced.

The test device according to one or more embodiments of the present invention comprises:

a chromatography support; and a housing accommodating the chromatography support, the housing enclosing an internal space where chromatography involving the use of the chromatography support is carried out, wherein the housing comprises:

a supporting part for supporting a container accommodating a liquid used for chromatography; and a perforation/incision part that perforates or incises the container supported by the supporting part to leak the liquid from the container into the internal space, the support is accommodated in the housing in a manner such that a part of the support is positioned between the supporting part and the perforation/incision part, and the supporting part comprises a container guide that guides the container from position A where the container faces the perforation/incision part through the part of the support to position B where the perforation/incision part perforates or incises the container together with the part of the support while the container is supported by the supporting part.

According to one or more embodiments of the present invention, a liquid used for chromatography accommodated in a container leaks from the container and efficiently comes into contact with the chromatography support.

The term "test device" used herein refers to an apparatus used for performing chromatography.

This description includes part or all of the content as disclosed in the description and/or drawings of Japanese Patent Application No. 2016-150452, which is a priority document of the present application.

According to one or more embodiments of the present invention, a test device that can reduce a risk of contamination when a liquid comes into contact with a chromatography support is provided.

According to one or more embodiments of the present invention, a test device that is provided with a simple mechanism for allowing a liquid used for chromatography to efficiently leak from the container accommodating the liquid is provided.

According to one or more embodiments of the present invention, a test device that is provided with a chromatography support accommodated in a housing and is easily visible from the outside of the housing is provided.

According to one or more embodiments of the present invention, a test device comprising a chromatography support accommodated in a housing that can allow a liquid used for chromatography to leak from the container accommodating the liquid and efficiently bring the liquid into contact with the support is provided.

BRIEF DESCRIPTION OF THE DRAWINGS

FIG. 7 schematically shows a cross sectional view of the test device according to one or more embodiments of the present invention.

FIG. 8 schematically shows a cross sectional view of the test device according to one or more embodiments of the present invention.

FIG. 14 shows a partial structure of the test device 1 provided with the housing 10 comprising an antireflection member 140 provided on an outer surface (an upper surface) 103a of the housing 10

FIG. 15A shows a perspective view of the upper housing member 10A constituting the first example of the housing 10 of the test device 1 provided with the visible light permeable protrusive part 103d outside of the upper wall 103c.

DETAILED DESCRIPTION OF THE EMBODIMENTS

Figure 1A:
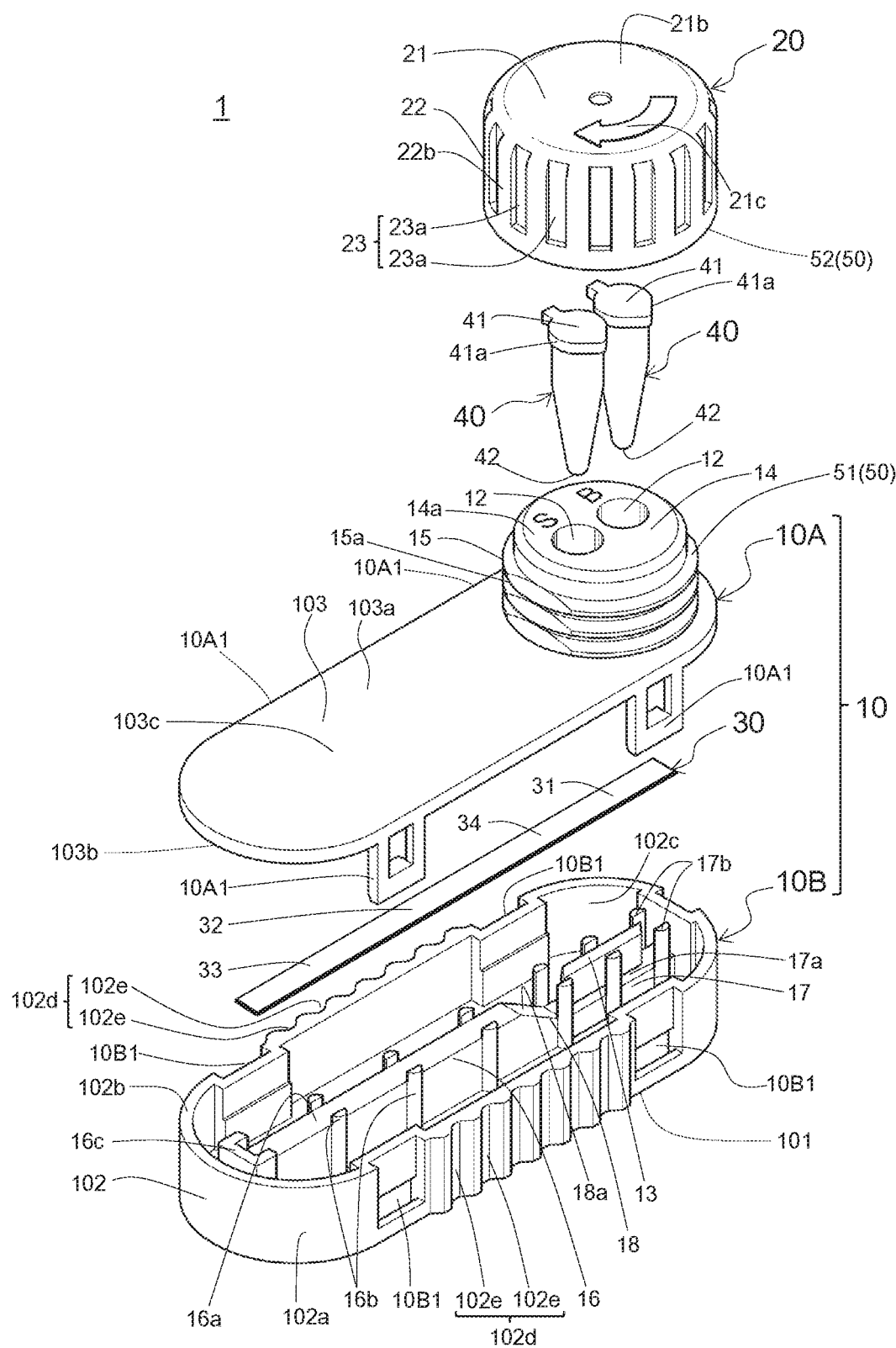
FIG. 1A shows an exploded perspective view of the test device according to one or more embodiments of the present invention.
Figure 1B:
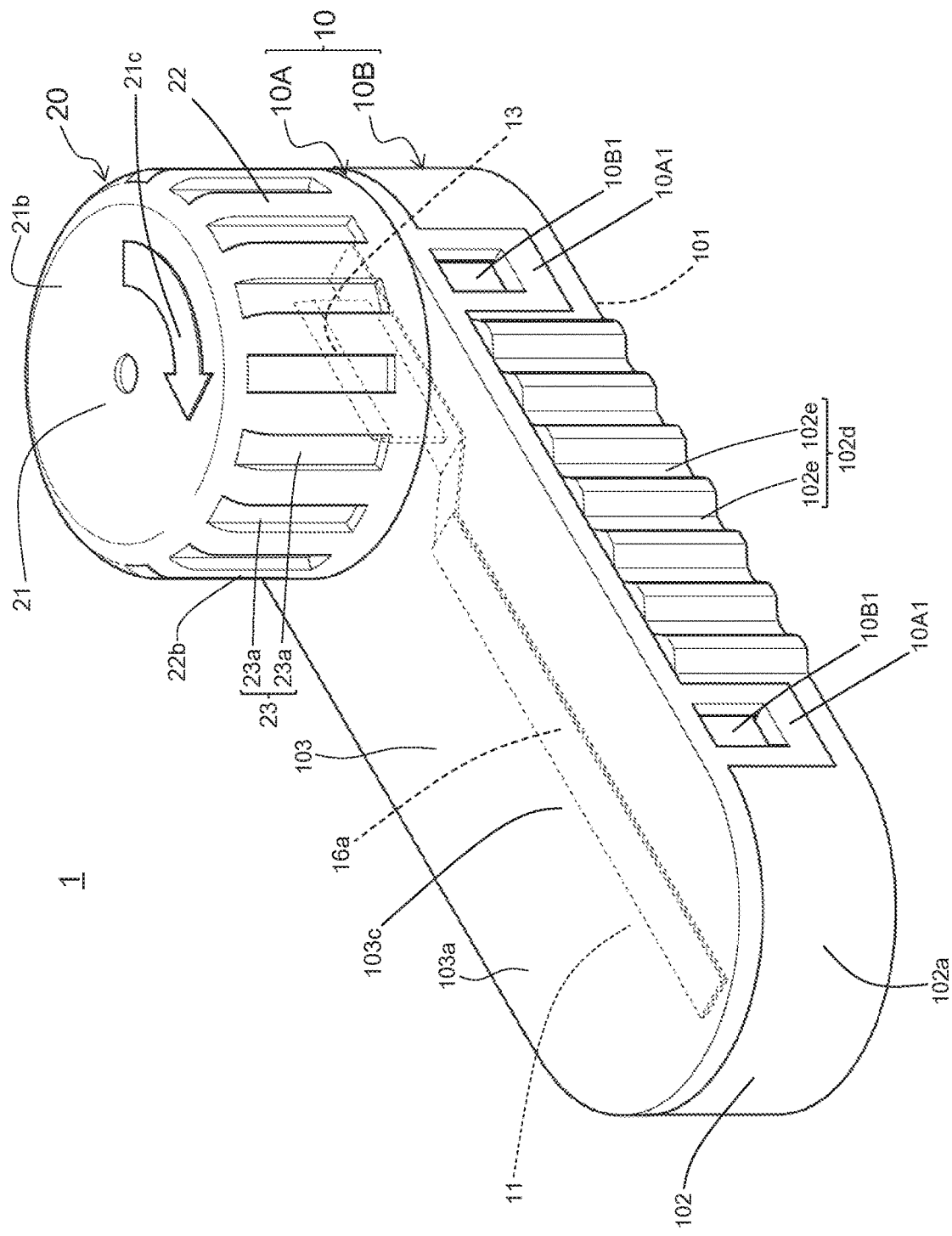
FIG. 1B shows a perspective view of the test device according to one or more embodiments of the present invention.
Figure 1C:
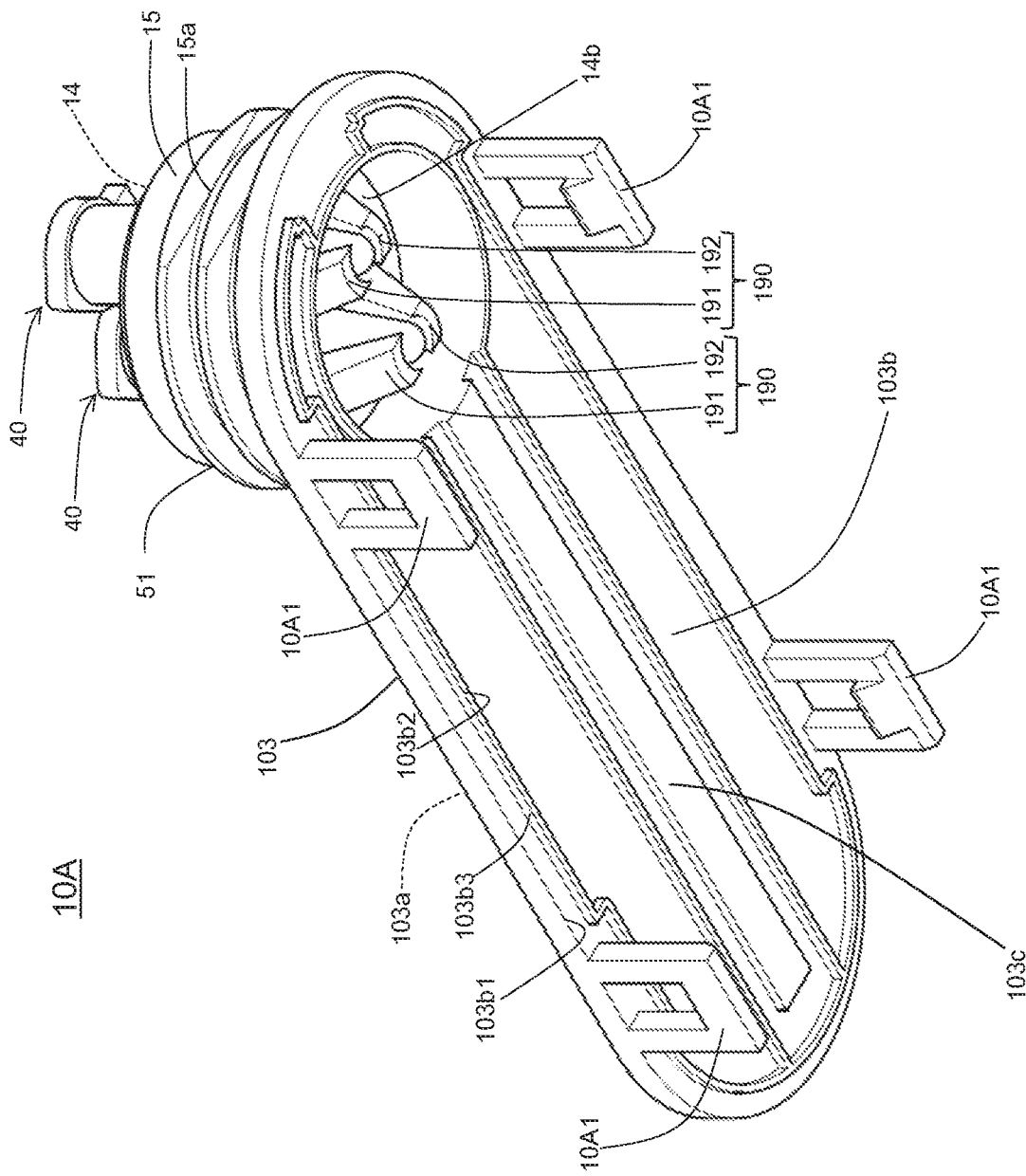
FIG. 1C shows a perspective view taken from the underneath of an upper housing member of the test device according to one or more embodiments of the present invention.

Hereafter, one or more embodiments of the present invention are described with reference to the drawings, although the scope of the present invention is not limited to one or more embodiments shown in the drawings.

FIRST EXAMPLE

The test device 1 according to the first example is described with reference to FIG. 1A to FIG. 5C.

The test device 1 according to the first example comprises a housing 10 and a lid 20. Materials constituting the housing 10 and the lid 20 are not particularly limited, and materials, such as resin and glass, can be adequately used.

The housing 10 encloses an internal space 11 in which chromatography involving the use of a chromatography support 30 is to be carried out.

The housing 10 also comprises a perforation/incision part 13 where containers 40 provided inside the internal space 11 are perforated or incised to allow liquids L to leak from the containers 40 into the internal space 11.

According to an example shown in the figure, the housing 10 is composed of an upper housing member 10A and a lower housing member 10B. The lower housing member 10B comprises a bottom wall 101 of the housing 10 and a side wall 102 rising upright from the periphery of the bottom wall 101. The upper housing member 10A comprises an upper wall 103 of the housing 10, the hole-formed part 14 of the housing described below, and a lid-mounting part 15. In the upper wall 103 of the upper housing member 10A, a surface serving as an outer surface of the housing 10 in combination with the lower housing member 10B is designated as an upper surface 103a, and a surface serving as an inner surface of the housing 10 in combination with the lower housing member 10B is designated as a lower surface 103b. In the periphery of the upper wall 103 of the upper housing member 10A, four latching convex parts 10A1 protruding toward the lower surface 103b are formed, and four latching concave parts 1031 engaged with the latching convex parts 10A1 are formed on an outer surface 102 of the side wall 102 of the lower housing member 10B.

The upper edge 102b of the side wall 102 of the lower housing member 10B abuts against the peripheral area 103b1 of the lower surface 103b of the upper wall 103 of the upper housing member 10A when the upper housing member 10A is engaged with the lower housing member 10B. In addition, a protrusive part 103b2 is provided on the lower surface 103b of the upper wall 103 in such a manner that it is adjacent to the inner periphery along the peripheral area 103b1 and protrudes from the peripheral area 103b1. When the upper housing member 10A is engaged with the lower housing member 10B, the outer peripheral surface 103b3 of the protrusive part 103b2 on the lower surface 103b of the upper wall 103 of the upper housing member 10A abuts against an area adjacent to the upper edge 102b of the inner surface 102c of the side wall 102 of the lower housing member 10B. When the upper housing member 10A is engaged with the lower housing member 103 to form the housing 10, a liquid can be prevented from leaking from the boundary between the side wall 102 and the upper wall 103.

According to an example shown in the figure, the housing 10 is composed of two members (i.e., the upper housing member 10A and the lower housing member 103). Members constituting the housing 10 are not limited thereto, and the housing 10 may be composed of a single member or three or more members.

The housing 10 is provided with one or more holes 12 (two holes according to an example shown in the figure) through which the internal space 11 can communicate with the outside and one or more containers 40 (two containers according to an example shown in the figure) accommodating liquids L used for chromatography can be supported. The part of the housing 10 where the holes 12 are formed is designated as a hole-formed part 14.

The internal space 11 is enclosed in the housing 10. According to an example shown in the figure, the internal space 11 is communicated with the outside through the holes 12, 12 while other portions are closed.

In the internal space 11 of the housing 10, chromatography is carried out. A solid-phase chromatography support 30 is provided in the internal space 11. In the internal space 11, chromatography can be carried out when liquid L comes into contact with a part of the chromatography support 30.

Examples of liquid L include a sample liquid containing detection targets in a medium such as water, a developing liquid, and a liquid containing labeling agents in a medium such as water. Examples of sample liquids include sample liquids containing amplified products of nucleic acids. Examples of developing liquids include phosphate buffer, Tris buffer, Good's buffer, and SSC buffer. A developing liquid may further contain a surfactant. A liquid L may be a mixture containing one or more of a sample liquid, a developing liquid, and a liquid containing a labeling agent. Alternatively, a liquid containing a color reagent or a dye may be used as liquid L. In the drawings and descriptions provided below, liquids accommodated in a plurality of containers 40 and a liquid released into the internal space 11 are collectively referred to as "liquid L" and each liquid L accommodated in one of a plurality of containers 40 may be of different compositions. A container 40 that accommodates liquid L other than the sample liquid may be communicated with the hole 12 in advance.

The chromatography support 30 provided in the internal space 11 of the housing 10 is not limited, provided that it is a solid-phase support. A support composed of a resin, metal, polysaccharide, mineral, or other material may be used in the form of, for example, a membrane, film, unwoven fabric, plate, or gel. According to an example shown in the figure, a configuration of the chromatography support 30 is a thin and long membrane, although the configuration is not limited thereto. In one or more embodiments, the chromatography support 30 preferably has a porous structure. Specific examples of the chromatography support 30 include paper, a nitrocellulose membrane, a polyether sulfone membrane, a nylon membrane, various types of dehydrated gels (e.g., silica gel, agarose gel, dextran gel, and gelatin gel), silicon, glass, and resin.

In a part of the chromatography support 30, a capture substance for capturing detection targets can be provided. When detection targets contain nucleic acids, for example, nucleic acids hybridizing to such nucleic acids can be used as capture substances. When detection targets contain antigens or antibodies, antigens or antibodies immunologically reacting with such antigens or antibodies can be used as capture substances.

In one or more embodiments, it is preferable that detection targets be visually detectable on the chromatography support 30. For example, detection targets may be labeled with labeling agents enabling visual detection of the detection targets and developed on the chromatography support 30. Thus, the detection targets can be visually detected. Examples of labeling agents enabling visual detection include colored particles, dyes, and fluorescent substances. Examples of "colored particles" include metal (e.g., gold, silver, copper, and platinum) particles, latex particles containing metal nanorods, metal nanoplates, dyes, and fluorescent substances, and silica nanoparticles including dyes and fluorescent substances. A method for labeling detection targets with labeling agents enabling visual detection is not particularly limited. When detection targets contain nucleic acids, for example, labeling agents to which nucleic acids hybridizing to the nucleic acids of interest are ligated may come into contact with the detection targets. Thus, detection targets can be labeled with labeling agents. From the viewpoint of visual detection, at least a part of a wall surrounding the internal space 11 of the housing 10 may be preferably formed of a material through which a visible light can penetrate, so that the chromatography support 30 can be observed from the outside of the housing 10. In particular, a part 103c positioned to face the part of the upper wall 103 of the housing 10 where the chromatography support 30 is to be positioned may be preferably formed of a material through which a visible light can penetrate.

Figure 9:
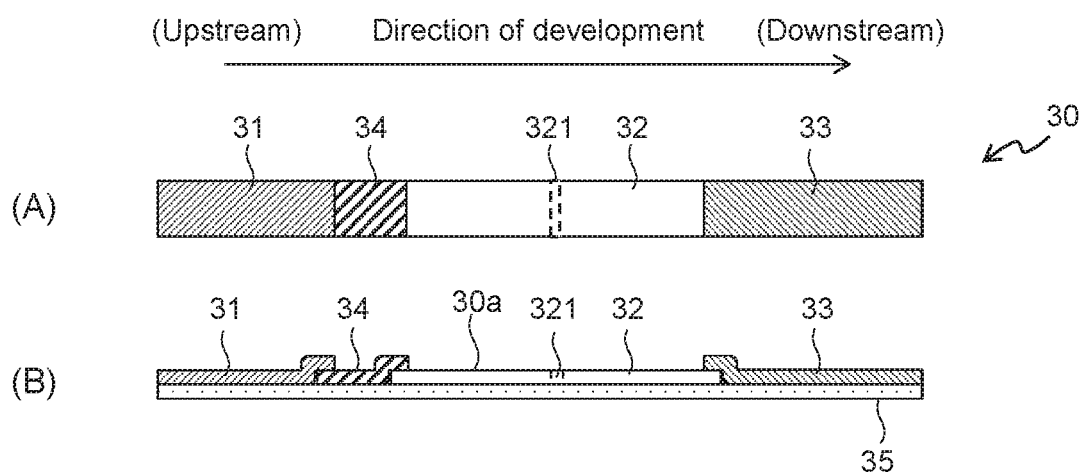
FIG. 9 shows a structure of a chromatography support that can be used in one or more embodiments of the present invention; wherein (A) shows a plane view and (B) shows a cross sectional view.

FIG. 9 shows the structure of the chromatography support 30 used in one or more embodiments. In one or more embodiments, the chromatography support 30 comprises a liquid receiver 31 and a detection part 32. The liquid receiver 31 is positioned at one end of the detection part 32 and liquid L is supplied thereto. In the detection part 32, detection targets are developed. An absorption pad 33 is positioned at another end of the detection pail 32. A labeling agent holder 34 for holding the labeling agents is positioned in a space between the liquid receiver 31 and the detection part 32. When liquid L supplied to the liquid receiver 31 contains detection targets, the detection targets are first labeled with labeling agents when passing through the labeling agent holder 34, and the detection targets then move to the detection part 32. When detection targets are labeled in advance or liquid L contains labeling agents, a labeling agent holder 34 is not necessary, the liquid receiver 31 can be located in a position adjacent to the detection part 32, or the liquid receiver 31 can be omitted. The detection part 32 comprises a capture region 321 on which the capture substance for capturing detection targets is provided. The liquid receiver 31, the labeling agent holder 34, the detection part 32, and the absorption pad 33 can be composed of the materials described above, so that these components can be used for the chromatography support 30. These components may be composed of the same or different members. The liquid receiver 31, the labeling agent holder 34, the detection part 32, and the absorption pad 33 can be positioned on a substrate 35, as shown in the figures. The substrate 35 can be composed of a resin, metal, polysaccharide, mineral, or other material. The substrate 35 can be partially or completely omitted. For example, a substrate equivalent to the lower portion of the liquid receiver 31 may be partially or completely omitted. Thus, flexibility of the liquid receiver 31 can be improved, and resistance caused when the container 40 is pushed toward the perforation/incision part can be reduced. Similar effects can also be attained with the use of a highly flexible substrate. A constitution of the chromatography support 30 is not limited to the constitution shown in FIG. 9, and a chromatography support with an adequate constitution can be selected in accordance with chromatography of interest.

Figure 10:
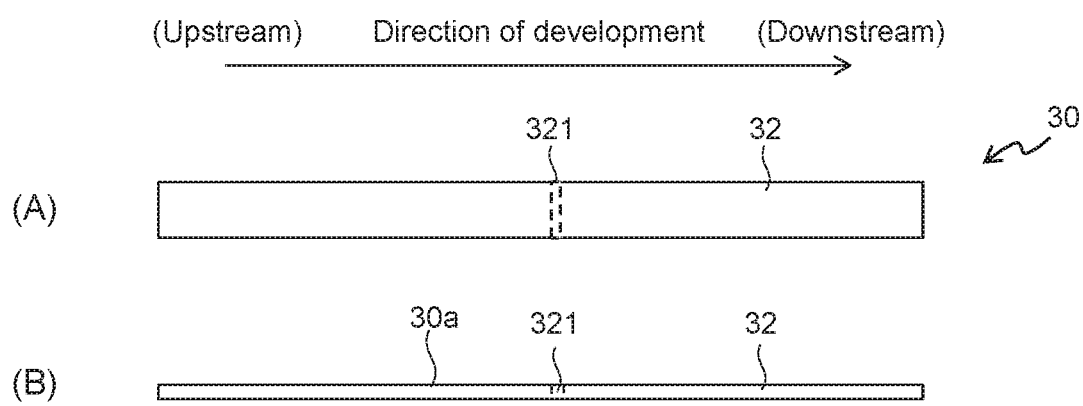
FIG. 10 shows a structure of another chromatography support that can be used in one or more embodiments of the present invention; wherein (A) shows a plane view and (B) shows a cross sectional view.

Another example of the chromatography support 30 is the chromatography support 30 consisting of the detection part 32 that does not comprise the liquid receiver 31, the labeling agent holder 34, the absorption pad 33, and the substrate 35, as shown in FIG. 10. The chromatography support 30 consisting of the detection part 32 and the substrate 35 that supports the detection part 32 can also be used (not shown).

In the internal space 11 of the housing 10 according to one or more embodiments, when the chromatography support 30 comprises the labeling agent holder 34, the liquid receiver 31 comes into contact with liquid L leaked from the container 40, but the detection part 32 and the absorption pad 33 are positioned to refrain from direct contact with the leaked liquid L. As described above, the labeling agent holder 34 can be omitted from the chromatography support 30 when, for example, liquid L contains labeling agents. Also, the chromatography support 30 consisting of the detection part 32 or the chromatography support 30 consisting of the detection part 32 and the substrate 35 can be used as described above. When the chromatography support 30 from which the labeling agent holder 34 is omitted, the chromatography support 30 consisting of the detection part 32 as shown in FIG. 10, or the chromatography support 30 consisting of the detection part 32 and the substrate 35 are used, liquid L leaked from the container 40 may be positioned to be in direct contact with the detection part 32. Hereafter, an example in which the chromatography support 30 is positioned in the internal space 11 of the housing 10 in such a manner that liquid L leaked from the container 40 comes into direct contact with the liquid receiver 31 but liquid L does not come into direct contact with the detection part 32 and the absorption pad 33 is described as a representative example. It should be noted that the present invention is not limited to this example.

In the internal space 11 of the housing 10, a support-mounting part 16 where the chromatography support 30 rising upright from the bottom wall 101 toward the internal space 11 is provided. The support-mounting part 16 is constituted in such a manner that the chromatography support 30 is positioned to face the part 103c of the upper wall 103 in a position closer to the upper wall 103 between the bottom wall 101 and the upper wall 103 in the direction in which the bottom wall 101 and the upper wall 103 of the housing face each other. The detection part 32 and the absorption pad 33 of the chromatography support 30 are provided on an upper surface 16a of the support-mounting part 16. In contrast, the liquid receiver 31 is positioned between the holes 12 and the perforation/incision part 13. The detection part 32 and the absorption pad 33 of the chromatography support 30 may be fixed to the upper surface 16a of the support-mounting part 16 with the aid of an adhesive agent or a pressure-sensitive adhesion tape. Liquid L leaked from the container 40 perforated or incised at the perforation/incision part 13 would not reach the upper surface 16a of the support-mounting part 16. When the housing 10 is disposed on a horizontal surface, specifically, the upper surface 16a is located in a position higher than the position where liquid L leaks from the container into the internal space 11. The upper surface 16a of the support-mounting part 16 has a planar configuration in accordance with a region comprising the detection part 32 and the absorption pad 33 of the chromatography support 30. According to an example shown in the figure, the upper surface 16a has a configuration with a longitudinal direction and a short-width direction. The support-mounting part 16 comprises a plurality of positioning protrusive parts in positions surrounding the upper surface 16a. The positioning protrusive parts prevent the migration of the chromatography support 30 in the direction along the upper surface 16a and positioning the chromatography support 30. Positioning protrusive parts are composed of the first positioning protrusive parts 16b positioned at both sides of the short-width direction of the upper surface 16a and the second positioning protrusive parts 16c positioned at one end of the upper surface 16a in the longitudinal direction.

According to an example shown in the figure, the number of holes 12 formed in the housing 10 is 2. The number thereof may be 1, it may be 3 or more, and it may be determined in accordance with the number of containers 40 accommodating liquids L used for chromatography of interest. When a sample liquid and a developing liquid are used as liquids L, for example, the number of holes 12 formed is 2. In such a case, it may be preferable that two holes 12 be formed in positions facing the position where the chromatography support 30 is provided in the internal space 11 along the direction of chromatographic development, a container 40 accommodating a sample liquid be inserted into the hole 12 located downstream in the direction of chromatographic development, and the container 40 accommodating a developing liquid be inserted into the hole 12 located upstream in the direction of chromatographic development. Thus, the amount of detection targets reaching the detection part 32 is increased, although the positions are not limited thereto. When there are 2 or more containers 40, configurations, color tones, and patterns of containers 40 may be different from each other, so that containers can be easily distinguished from each other. Each liquid L accommodated in each container 40 may be colored to have a color tone different from that of liquid L to be contained in another container. When two or more containers 40 having different configurations are used, holes 12 may have different configurations to fit the configurations of relevant containers.

The lid 20 is mounted on the housing 10 to cover the hole-formed part 14 of the housing 10. When a liquid is present between the hole-formed part 14 of the housing and the lid 20, the lid 20 covers the hole-formed part 14 of the housing, so as to prevent the liquid from leaking to the outside of the test device 1 under normal conditions.

At least either one of the housing 10 and the lid 20 comprises a guide 50 that guides the lid 20 to the housing 10, so that the lid 20 can migrate from the first position to the second position described below while covering the hole-formed part 14 of the housing 10. The term "guide" used herein may also be referred to as a "lid guide."

Figure 4A:
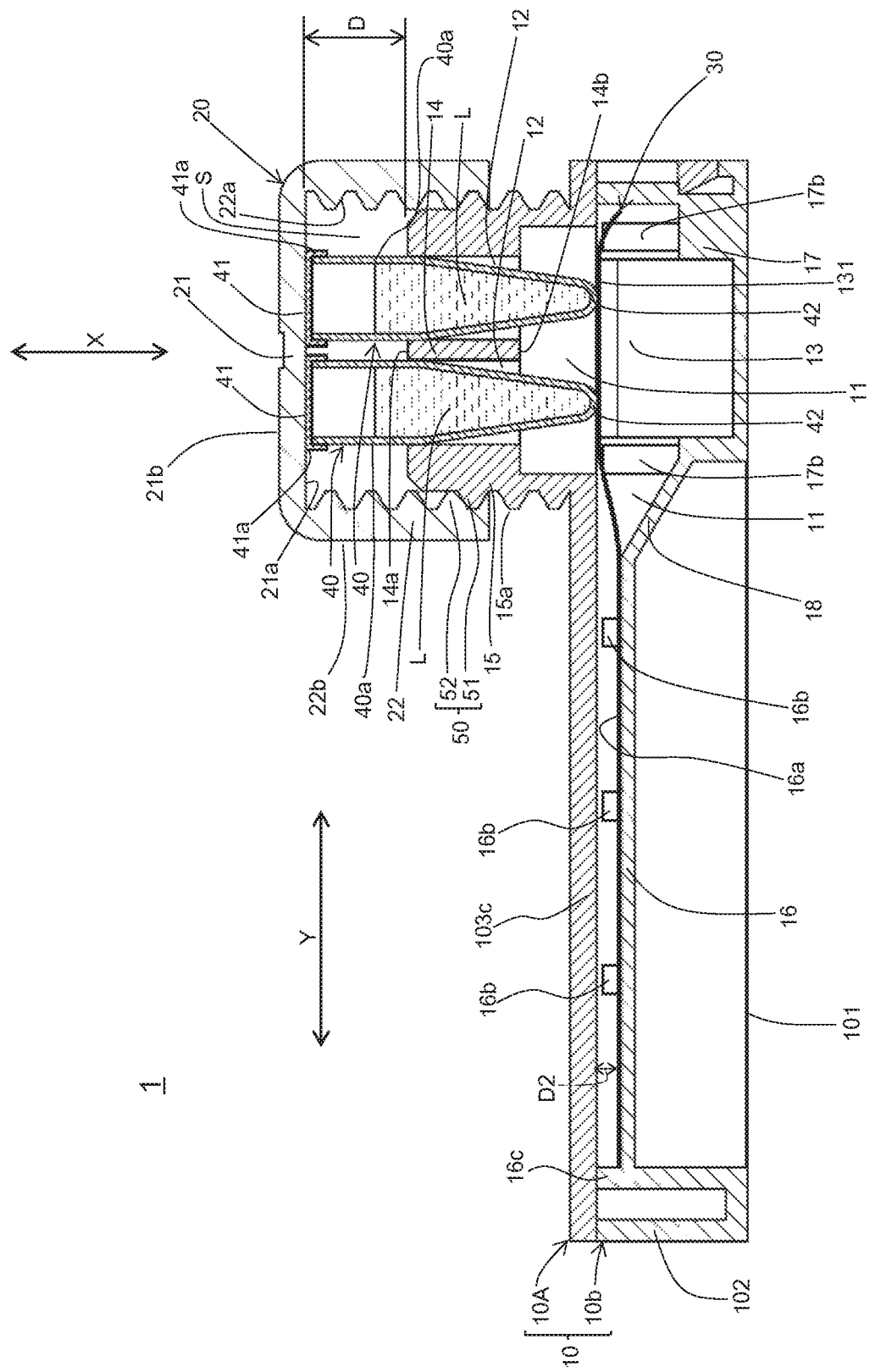
FIG. 4A schematically shows a cross section of the test device according to one or more embodiments of the present invention in a longitudinal direction in which the lid is positioned in the first position with respect to the housing.
Figure 5A:
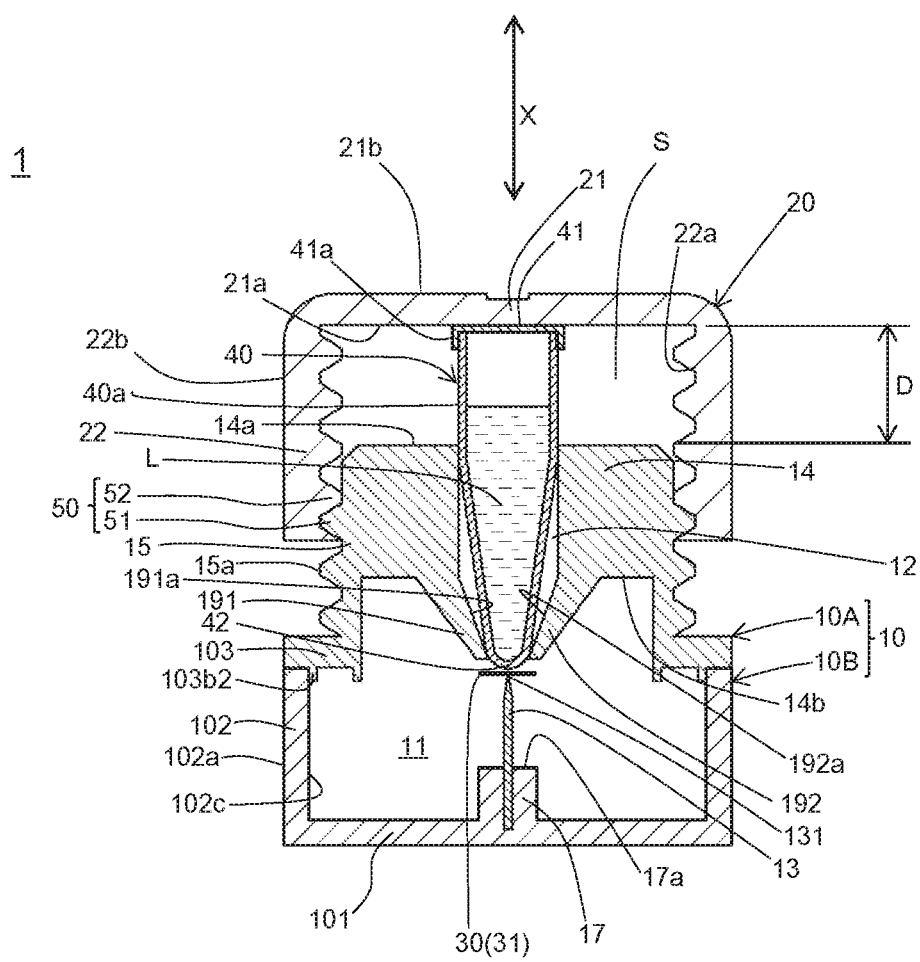
FIG. 5A schematically shows an end plane of the test device according to one or more embodiments of the present invention in a short-width direction in which the container is inserted into a hole and the lid is positioned in the first position with respect to the housing.

The term "the first position" refers to a position of the lid 20 relative to the housing 10, such that the lid 20 covers the hole-formed part 14 of the housing 10 while keeping a space S therebetween, so as to designate the distance D between the hole-formed part 14 of the housing 10 and a main lid part 21 facing the hole-formed part 14 of the housing of the lid 20 as the first distance. FIG. 4A and FIG. 5A schematically shows the test device 1 according to one or more embodiments in which, while the containers 40 are inserted into and supported by the holes 12 of the housing 10, the hole-formed part 14 of the housing 10 is covered by the lid 20, and the position of the lid 20 relative to the housing 10 is the first position.

Figure 4B:
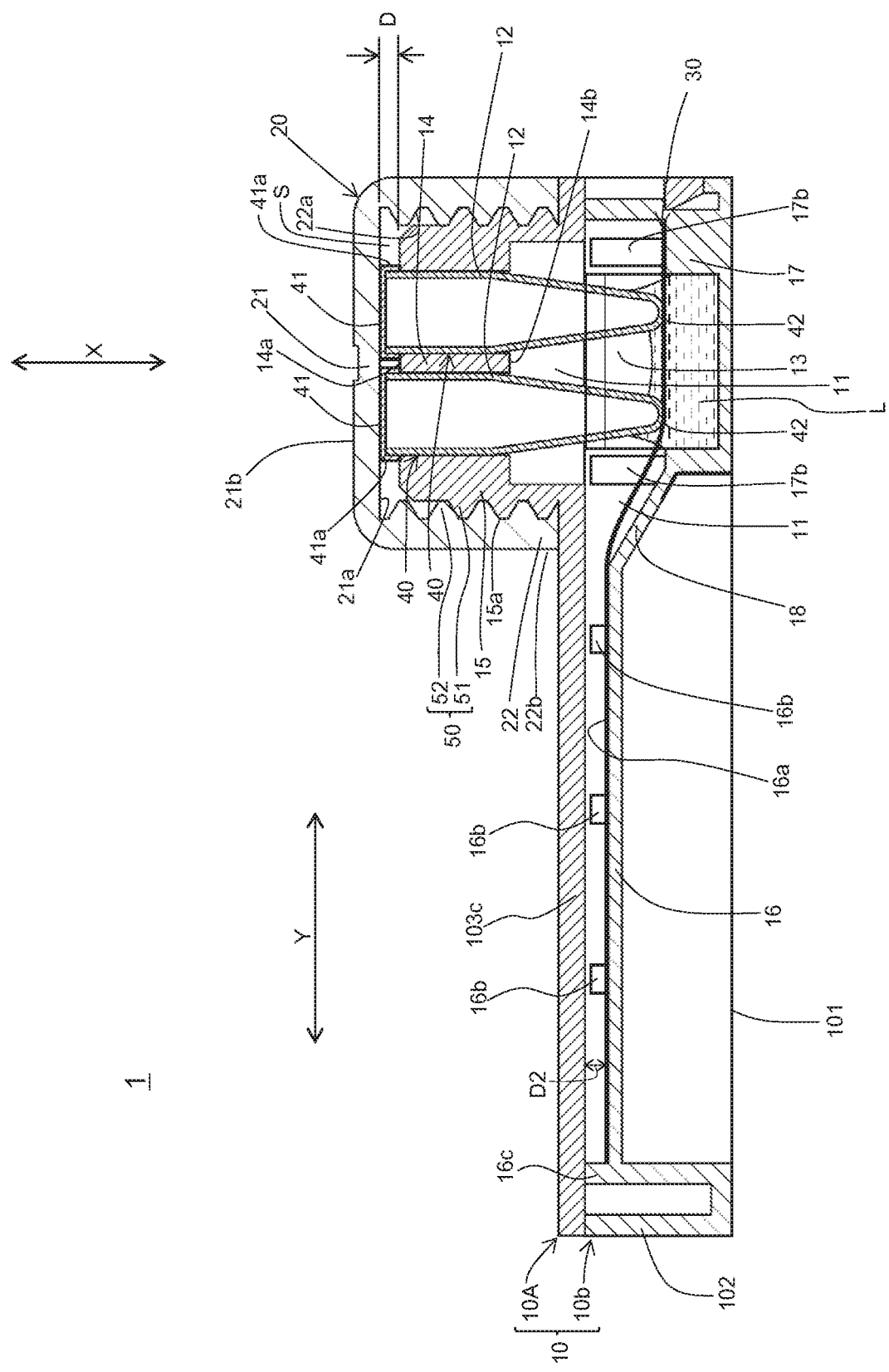
FIG. 4B schematically shows a cross section of the test device according to one or more embodiments of the present invention in a longitudinal direction in which the lid is positioned in the second position with respect to the housing.
Figure 5B:
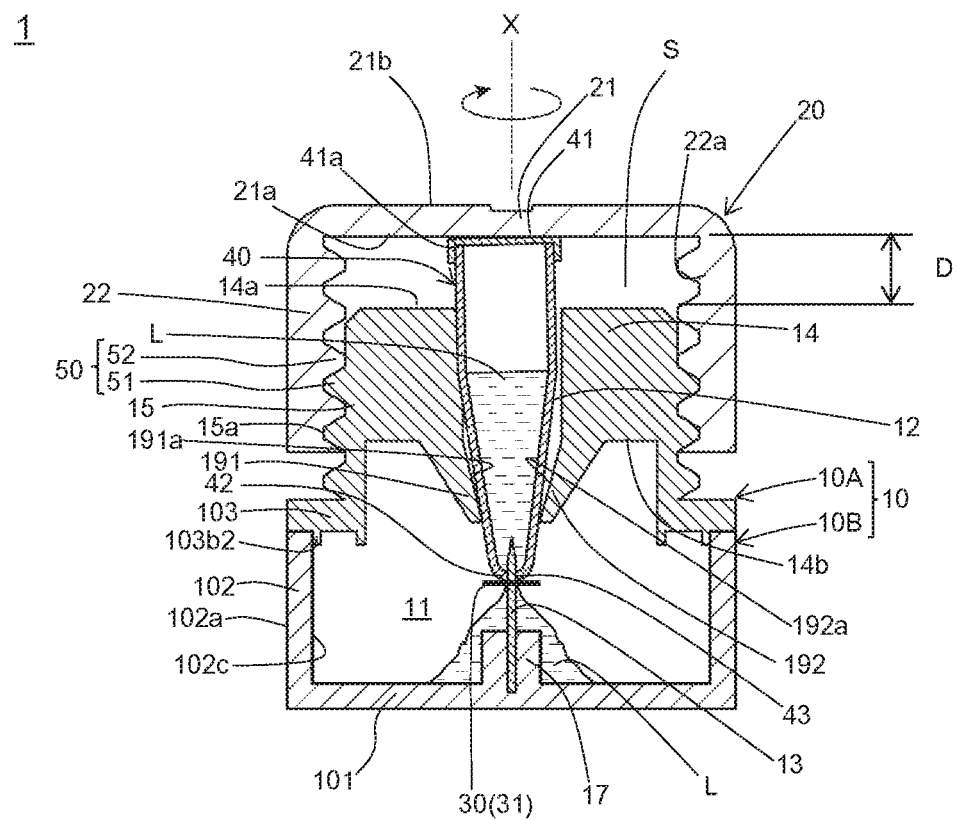
FIG. 5B schematically shows an end plane of the test device according to one or more embodiments of the present invention in a short-width direction in which the container is inserted into a hole and the lid is allowed to migrate from the first position to the second position toward the housing.
Figure 5C:
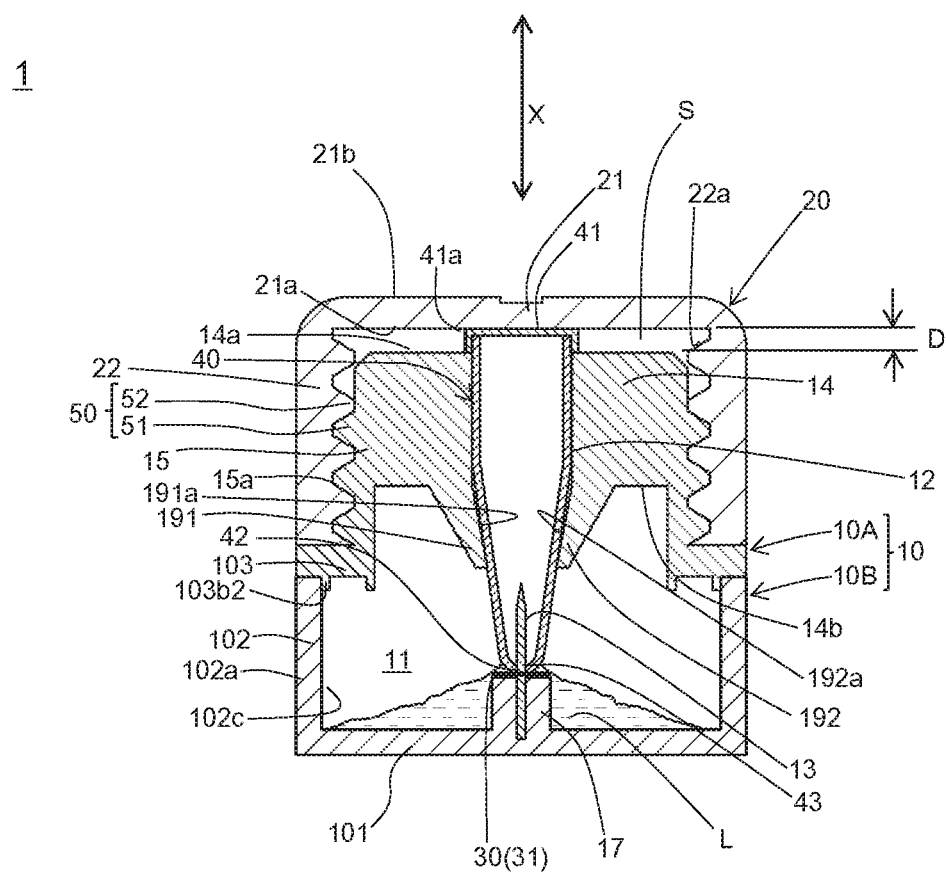
FIG. 5C schematically shows an end plane of the test device according to one or more embodiments of the present invention in a short-width direction in which the container is inserted into a hole and the lid is positioned in the second position with respect to the housing.

The term "the second position" refers to a position of the lid 20 relative to the housing 10, such that the lid 20 covers the hole-formed part 14 of the housing 10, so as to adjust the distance D as the second distance, which is shorter than the first distance. FIG. 4B and FIG. 5C schematically show the test device 1 according to one or more embodiments in which, while the containers 40 are inserted into and supported by the holes 12, 12 of the housing 10, the hole-formed part 14 of the housing 10 is covered by the lid 20, and the position of the lid 20 is the second position.

The term "the distance D" refers to a distance between the outer surface 14a of the hole-formed part 14 of the housing facing the lid 20 and the inner surface 21 of the main lid part 21 of the lid 20 facing the hole-formed part 14 of the housing in a direction X in which the outer surface 14a and the inner surface 21a face each other. When such distance varies depending on sites, the longest distance is designated as the distance D.

According to one or more embodiments, the lid 20 is composed of the main lid part 21 and the peripheral wall part 22 starting from the outer periphery of the main lid part 21 extending toward the inner surface 21a of the main lid part 21.

According to one or more embodiments, the hole-formed part 14 of the housing 10 is provided in a position protruded outwardly from the upper wall 103, and the hole-formed part 14 of the housing is connected to the upper wall 103 by the lid-mounting part 15 on which the lid 2 is to be mounted that surrounds the hole-formed part 14 of the housing.

According to one or more embodiments, the guide 50 is composed of a housing-side screw-engagement part 51 provided on the outer peripheral surface 15a in the lid-mounting part 15 of the housing 10 and a lid-side screw-engagement part 52 provided on the inner peripheral surface 22a in the peripheral wall part 22 of the lid 20 that can engage with the housing-side screw-engagement part 51. When the lid 20 mounted on the housing 10 in the first position is allowed to revolve with the aid of the housing-side screw-engagement part 51 and the lid-side screw-engagement part 52 around the axis along the direction X in which the hole-formed part 14 of the housing 10 faces the lid 20, the main lid part 21 of the lid 20 can migrate along the direction X toward the hole-formed part 14 of the housing 10. The guide 50 can allow the lid 20 to migrate from the first position to the second position of the housing 10. During the migration, the hole-formed part 14 of the housing remains covered by the lid 20, and leaking of a liquid can be prevented. The guide 50 can be constructed in such a manner that liquid L cannot substantially pass through a space between the housing 10 and the lid 20.

The screw-engagement part composed of the housing-side screw-engagement part 51 and the lid-side screw-engagement part 52 is an example of the power boost mechanism that converts a power of allowing the lid 20 to revolve around the direction X into a power of allowing the lid 20 to migrate toward the hole-formed part 14 of the housing 10 along the direction X. As the diameter of the screw-engagement part is increased, the lid 20 can migrate to the hole-formed part 14 of the housing 10 more efficiently. In order to allow the lid 20 to revolve more easily, as shown in the figure, it may be preferable that an anti-slip area 23 comprising a plurality of concave grooves 23a with gaps therebetween that extend in the direction X be provided on the outer surface 22b of the peripheral wall part 22 of the lid 20. On the outer surface 21b of the main lid part 21 of the lid 20, a label 21c that enables visual observation of the revolving direction can be provided.

The guide 50 is not limited to the screw-engagement part shown in the figure, and one or more embodiments may be employed. According to one or more embodiments of the guide 50, for example, screw-engagement parts are not provided on the outer peripheral surface 15a of the lid-mounting part 15 of the housing 10 and on the inner peripheral surface 22a of the peripheral wall part 22 of the lid 20. While the outer peripheral surface 15a of the lid-mounting part 15 of the housing 10 abuts against the inner peripheral surface 22a of the peripheral wall part 22 of the lid 20, the lid 20 is guided from the first position to the second position while sliding to the housing 10. According to one or more embodiments, screw-engagement parts are not provided on the outer peripheral surface 15a of the lid-mounting part 15 of the housing 10 and on the inner peripheral surface 22a of the peripheral wall part 22 of the lid 20. While the outer peripheral surface 15a of the lid-mounting part 15 of the housing 10 abuts against the inner peripheral surface 22a of the peripheral wall part 22 of the lid 20 through one or more seal members disposed therebetween, the lid 20 is guided from the first position to the second position to the housing 10. A seal material can be made of a material capable of elastic deformation, such as rubber. A seal material may be fixed to either one of the outer peripheral surface 15a of the lid-mounting part 15 of the housing 10 and the inner peripheral surface 22a of the peripheral wall part 22 of the lid 20. Also, a lock mechanism that locks the lid 20, which had migrated from the first position to the second position, in the second position and prevents the lid 20 from returning back to the first position or from being released from the housing 10 may be provided.

Figure 3:
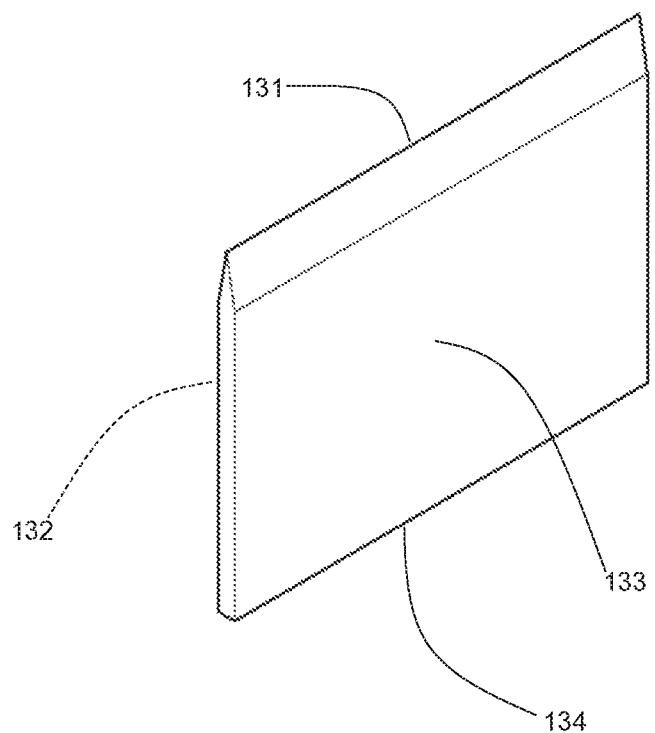
FIG. 3 shows a perspective view of a blade (a perforation/incision part) of the test device according to one or more embodiments of the present invention.

The perforation/incision part 13 perforates or incises the containers 40 to leak liquids L from the containers 40 into the internal space 11. In one or more embodiments, a blade that incises the containers 40 as shown in FIG. 3 is used as the perforation/incision part 13 (indicated as the "blade 13" when the perforation/incision part 13 is specified as the blade). The blade 13 shown in FIG. 3 is of a double-edge structure, such that both the lateral surface 132 and the lateral surface 133 incline in the vicinity of the edge 131 and intersect with each other at the edge 131, although the blade is not limited thereto. Alternatively, a blade of a single-edge structure, such that one of the two lateral surfaces 132 and 133 inclines, the other remain flat, and such surfaces intersect with each other at the edge 131 may be employed. Also, the perforation/incision part 13 is not limited to the blade. An example of the perforation/incision part 13 other than the blade is a needle that perforates the containers 40. According to one or more embodiments, a plurality of containers 40 are incised at a single perforation/incision part 13, the construction is not limited thereto, and a plurality of perforation/incision parts 13 may be provided in accordance with the relevant containers. Materials constituting the perforation/incision part 13 are not particularly limited, provided that such materials can provide sufficient strength to perforate or incise the containers 40. Examples thereof include metals, such as steels and aluminum, ceramics, and resin.

The perforation/incision part 13 is provided inside the internal space 11 of the housing 10. According to one or more embodiments, the perforation/incision part 13 is provided on the bottom wall 101 facing the holes 12 inside the internal space 11 of the housing 10, although the perforation/incision part 13 is not limited thereto. In the housing 10, a fixing part 17 provided upright from the bottom wall 101 toward the hole-formed part 14 of the housing is provided inside the internal space 11, and a perforation/incision part 13 is fixed to the housing 10 through the fixing part 17. According to one or more embodiments, the fixing part 17 is arranged on the same line with the support-mounting part 16 in the bottom wall 101. When the test device 1 according to one or more embodiments is placed on a horizontal surface, the upper surface 17a of the fixing part 17 is located in a position lower than the upper surface 16a of the support-mounting part 16. The support-mounting part 16 is connected to the fixing part 17 with the connector 18 provided upright from the bottom wall 101 in the internal space 11. The upper surface 16a of the support-mounting part 16 is connected to the upper surface 17a of the fixing part 17 through the upper surface 18a of the connector 18 inclined from the upper surface 16a of the support-mounting part 16 toward the upper surface 17a of the fixing part 17. On both sides of the fixing part 17 that fixes the perforation/incision part 13 in the short-width direction of the upper surface 17a, third positioning protrusive parts 17b are provided. In accordance with the migration of the lid 20 from the first position to the second position, the perforation/incision part 13 fixed by the fixing part 17 and the liquid receiver 31 of the chromatography support 30 provided between the holes 12 and 12 migrate toward the fixing part 17. In such a case, migration of the liquid receiver 31 is restricted to the direction of the migration of the lid 20.

The holes 12 formed in the hole-formed part 14 of the housing 10 are through holes that allow communication between the internal space 11 and the outside of the housing 10. The configuration of the holes 12 is not particularly limited, provided that the containers 40 can be inserted thereinto and supported thereby in a through-hole direction, and the containers 40 can be guided to move toward the perforation/incision part 13 as the lid 20 migrates.

As the container 40, a container that can accommodate liquid L used for chromatography, that can be inserted into and supported by the hole 12 of the housing 10, and that can be perforated or incised by the perforation/incision part 13 can be used. The container 40 is typically a resin container. As the container 40, a tubular container that extends in one direction with one end being closed and the other end having an opening may be preferable. The example shown in the figure, specifically, employs a container that has an opening 41a at the outer end 41 positioned outside of the housing 10 and that is closed at the inner end 42 positioned inside of the housing 10 when the containers are inserted into the holes 12. An example of such container 40 is a microtube used for nucleic acid amplification or biochemical testing.

The hole-formed part 14 of the housing comprises, at a position surrounding a relevant hole 12, an elastic member 190 that urges the container 40, which is inserted into and supported by the hole 12, against the axis along the through-hole direction of the hole 12 and retains the position of the container 40 in the hole 12. Specifically, the elastic member 190 is composed of a pair of elastic supporting pieces 191 and 192 protruded from a pair of positions facing each other in the vicinity of the hole 12 on the inner surface 14b facing the internal space 11 of the hole-formed part 14 of the housing toward the internal space 11. The pair of elastic supporting pieces 191 and 192 are positioned in a manner such that a surface 191a of an elastic supporting piece 191 faces a surface 192a of the other elastic supporting piece 192. The surface 191a of an elastic supporting piece 191 and the surface 192a of the other elastic supporting piece 192 are formed in a manner such that the distance therebetween becomes smaller as the distance along the direction X from the inner surface 14b of the hole-formed part 14 of the housing becomes larger. The pair of elastic supporting pieces 191 and 192 flank the container 40 inserted into the hole 12 and urge the container against the axis along the through-hole direction of the hole 12 to retain the position. The pair of elastic supporting pieces 191 and 192 are capable of elastic deformation. As the container 40 is pushed toward the perforation/incision part 13, the elastic supporting pieces are pushed to open in accordance with the configuration of the container 40. As shown in the figure, accordingly, the position of the container 40 can be stably maintained even with the use of the container 40 configured to have an increasing width from the inner end 42 toward the outer end 41. As long as the elastic supporting pieces 191 and 192 are capable of elastic deformation, a container 4C) with a different width can be supported stably. According to one or more embodiments, the positions of the containers 40 inserted into the holes 12 can be maintained with the aid of the elastic member 190 composed of the pair of elastic supporting pieces 191 and 192. Thus, the position of the container 40 with respect to the perforation/incision part 13 can be stabilized, and the amount of liquid L leaking from the container 40 can be stabilized.

Subsequently, the movement of the lid 20 from the first position to the second position, while allowing the containers 40 accommodating liquids L to be inserted into and supported by the holes 12 of the housing 10 of the test device 1 according to one or more embodiments, by mounting the lid 20 on the housing 10 through the lid-mounting part 15, and covering the hole-formed part 14 of the housing 10 with the lid 20 is described with reference to FIG. 4A to FIG. 5C.

In order to provide the lid 20 in the first position, as shown in FIG. 4A and FIG. 5A, the containers 40 are inserted into and supported by the holes 12 of the housing 10, and the lid 20 is mounted on the lid-mounting part 15 surrounding the hole-formed part 14 of the housing 10. In this case, the housing-side screw-engagement part 51 on the outer peripheral surface 15a of the lid-mounting part 15 of the housing 10 is allowed to partially engage with the lid-side screw-engagement part 52 on the inner peripheral surface 22a of the peripheral wall part 22 of the lid 20. Thus, the hole-formed part 14 of the housing 10 and the outer regions 40a of the container 40 are covered by the lid 20. In the first position, the containers 40 are not perforated or incised at the perforation/incision part 13. When the lid 20 is positioned in the first position, specifically, the container 40 is located between the main lid part 21 of the lid 20 and the perforation/incision part 13 facing each other. The inner ends 42 of the containers 40 may not be in contact with the edge 131 of the perforation/incision part 13. Alternatively, they may be in contact with each other, but the containers are not perforated or incised. Specifically, the outer portions 40a of the containers 40 and the hole-formed part 14 of the housing are covered by the lid 20 before liquids L are allowed to leak from the containers 40. A space S is formed between the hole-formed part 14 of the housing 10 and the lid 20. A space S is communicated with the internal space 11 of the housing 10 through the holes 12. While the entire space S is a closed space within the test device 1, it is not necessarily airtight. The height of the space S is the distance D described above, and the distance D is the first distance described above. Before liquids L are allowed to leak from the containers 40, the entire containers 40 are enclosed in a closed space. Thus, dispersion of liquids L, from the test environment can be effectively suppressed.

In one or more embodiments of the present invention, while the container is inserted into and supported by at least one hole of the housing described above, the hole-formed part of the housing is covered by the lid, and the lid is positioned in the first position with respect to the housing. In that state, a part of the lid facing the hole-formed part of the housing may or may not abut against the outer portion protruded from the one or more holes of the container toward the lid. When these components do not abut against each other, the part of the lid facing the hole-formed part of the housing and the outer portion protruded from the one or more holes of the container toward the lid may begin to abut against each other while the lid migrates from the first position to the second position toward the housing. According to the examples shown in FIG. 4A and FIG. 5A, specifically, a main lid part 21 of the lid 20, which faces the hole-formed part 14 of the housing, abuts against the outer end 41 of the container 40 when the lid 20 is in the first position, although the present invention is not limited to such example. Alternatively, a given main lid part 21 of the lid 20 may be located separately from the outer end 41 of the container 40, and the main lid part 21 may begin to abut against the outer end 41 of the container 40 while the lid 20 migrates from the first position to the second position.

According to the examples shown in FIG. 4A and FIG. 5A, when the lid 20 is positioned in the first position, the liquid receiver 31 of the chromatography support 30 is located between the inner end 42 of the container 40 and the edge 131 of the perforation/incision part 13. However, the liquid receiver 31 is not necessarily positioned in this position, but it may be positioned in a manner such that it can come into contact with the leaked liquid L when liquid L leaks into the internal space 11.

Subsequently, the lid 20 is allowed to migrate from the first position to the second position toward the housing 10. FIG. 5B schematically shows the condition during the process of migration. In this process, the main lid part 21 of the lid 20 abuts against the outer end 41 of the container 40, the container 40 is pushed toward the perforation/incision part 13, the container 40 is perforated or incised at the perforation/incision part 13 (incised according to an example shown in the figure), and liquid L then leaks into the internal space 11. During the process of migration, the lid 20 migrates while covering the hole-formed part 14 of the housing 10. In the internal space 11, accordingly, liquid L leaked from the container 40 can be suppressed to disperse outside the test device 1.

In this process, in addition, the main lid part 21 of the lid 20 abuts against the outer end 41 of the container 40. As shown in the figure, accordingly, an opening 41a of a microtube would not open when a microtube having an opening 41a at the outer end 41 is used as the container 40. This can suppress the opening 41a of the microtube to open, even when the container 40 is pushed against the perforation/incision part 13 and the pressure inside the container is increased.

According to one or more embodiments, the guide 50 is composed of the housing-side screw-engagement part 51 and the lid-side screw-engagement part 52, the lid 20 mounted on the housing 10 in the first position revolves around the direction X, and the main lid part 21 of the lid 20 migrates along the direction X toward the hole-formed part 14 of the housing 10. As a result, friction occurs between the main lid park 21 of the lid 20 and the outer end 41 of the container 40, a torsion is applied in a direction approximately vertical to the direction X, and the container 40 is pushed along the direction X toward the perforation/incision part 13. FIG. 5B schematically shows that the container 40 is pushed into the perforation/incision part 13 with some inclination from the direction X as the lid 20 revolves. This opens the leakage port 43 formed via perforation or incision of the container, liquid L is effectively leaked, and chromatography conditions can be thus stabilized.

As described above, the containers 40 are each pushed into the perforation/incision part 13 while the positions thereof in the holes 12 are maintained by the pair of elastic supporting pieces 191 and 1232. Thus, the position thereof with respect to the perforation/incision part 13 can be kept stable, the amount of liquid L leaked from the container can be kept constant, and chromatography conditions can be thus stabilized.

Liquids L leaks from the containers 40 through the leakage port 43 to regions on the fixing part 17 of the perforation/incision part 13 and in the vicinity of the fixing part 17. According to one or more embodiments, a reservoir space for storing liquid L may be separately provided in the internal space 11.

According to one or more embodiments, the liquid receiver 31 of the chromatography support 30 is pushed into the perforation/incision part 13 by the inner end 42 of the container 40, the liquid receiver 31 is perforated or incised together with the container 40 at the edge 131 of the perforation/incision part 13, and the liquid receiver 31 approaches the fixing part 17. The present invention is not limited to one or more embodiments, and the liquid receiver 31 of the chromatography support 30 may be positioned in any position, provided that it can come into contact with liquid L leaked in the internal space 11.

FIG. 4B and FIG. 5C each schematically show the conditions in which the lid 20 is further allowed to migrate to the second position toward the housing 10. In the second position, a large amount of liquid 1, leaks, the liquid receiver 31 of the chromatography support 30 is sufficiently soaked in the leaked liquid L, and development thereof on the chromatography support 30 proceeds. According to one or more embodiments, the third positioning protrusive parts 17b are provided in positions flanking the liquid receiver 31 of the chromatography support 30 in a width direction. Thus, movement of the liquid receiver 31 is limited to one direction along the direction X in which the lid 20 moves from the first position to the second position. Thus, the liquid receiver 31 can be soaked in liquid L with certainty. According to one or more embodiments, as shown in FIG. 5B, the liquid receiver 31 of the chromatography support 30 begins to be soaked in liquid L while the lid 20 migrates from the first position to the second position, although the constitution is not limited thereto. Alternatively, the liquid receiver 31 may be constituted in a manner such that the liquid receiver 31 is first soaked in liquid L when the housing 20 is positioned in the second position.

When the lid 20 is positioned in the second position with respect to the housing 10, the distance D between the outer surface 14a of the hole-formed part 14 of the housing and the inner surface 21a of the main lid part 21 of the lid 20 facing the outer surface 14a is the second distance, which is smaller than the first distance. According to examples shown in FIG. 4B and FIG. 5C, the second distance is larger than 0, and the space S remains between the outer surface 14a of the hole-formed part 14 of the housing and the inner surface 21a of the main lid part 21 of the lid 20. It should be noted that the present invention is not limited to such example, the second distance may be zero, and the space S may not be present.

In the second position, the lid 20 covers the hole-formed part 14 of the housing 10. Thus, liquid L leaked into the internal space 11 can be prevented from dispersing to the outside of the test device 1.

Figure 2:
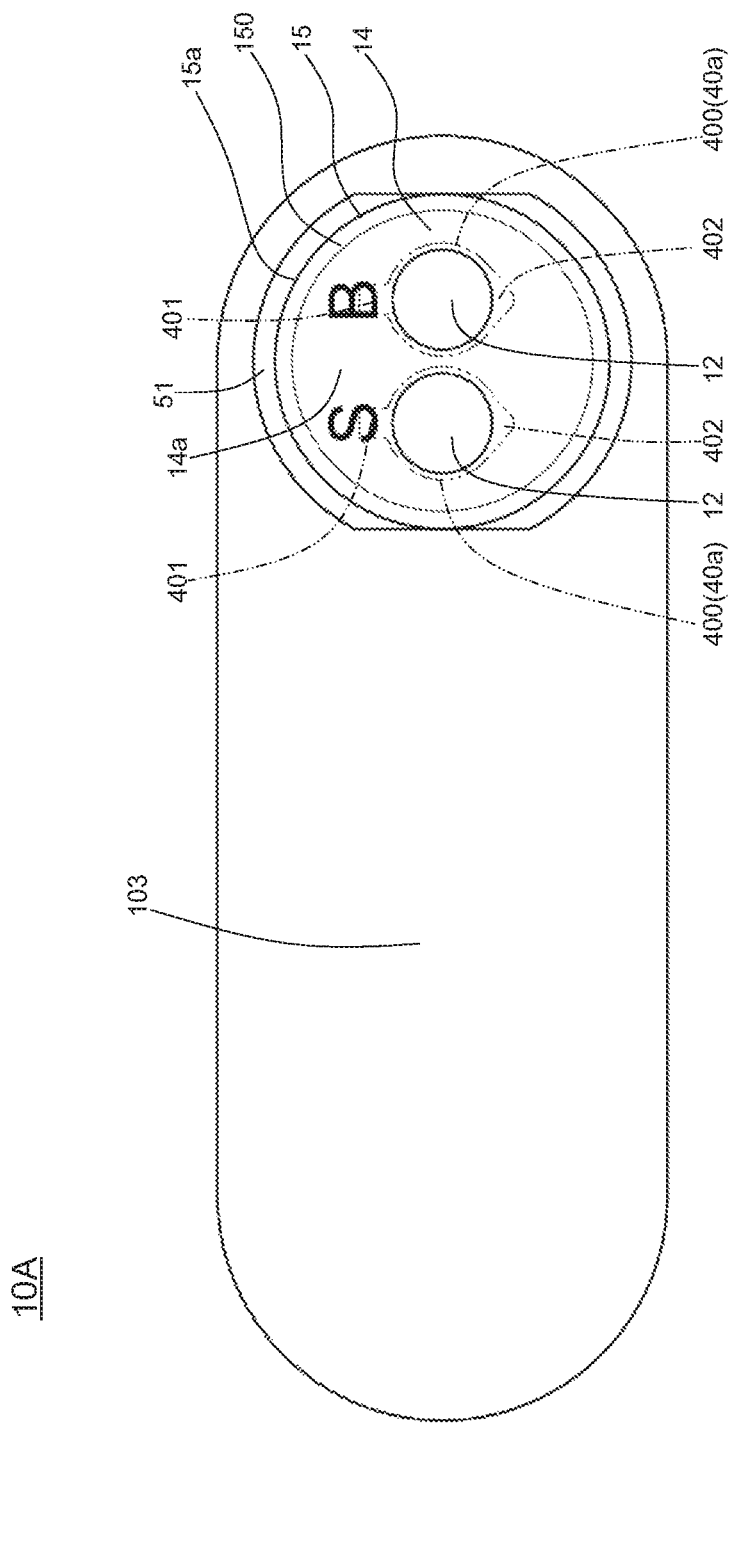
FIG. 2 shows a plane view of an upper housing member of the test device according to one or more embodiments of the present invention.

The test device 1 according to one or more embodiments is constructed in a manner such that the lid-mounting part 15 surrounds the hole-formed part 14 of the housing, as described above. As shown in FIG. 2, the housing 10 is constituted in a manner such that the profile 400 of the outer portion 40a of the container 40 is enclosed in the inner periphery 150 of the lid-mounting part 15, when the container 40 inserted into and supported by the hole 12 is viewed from the outside of the housing 10 in the through-hole direction of the hole 12. Because of this constitution, the lid 20 is easily mounted while the containers 40 are inserted into the holes 12 of the housing 10, and migration of the lid 20 from the first position to the second position is less likely to be blocked by the outer portion 40a of the container 40.

According to one or more embodiments, the housing 10 is constituted in a manner such that the profiles 400 of the outer portions 40a of the containers 40 are enclosed in the inner periphery 150 of the lid-mounting part 15 while the containers 40 remain inserted into and supported by the holes 12, regardless of the direction of the containers 40 in the holes 12. Thus, the lid 20 can be mounted on the lid-mounting part 15 without causing interference between the lid 20 and the outer portion 40a of the container 40 when the container 40 is inserted into the hole 12 of the housing 10, regardless of the direction of the container 40 in the hole 12. This enables a user to operate the test device according to one or more embodiments, regardless of the direction of the container. In particular, the container 40 comprising an opening 41a at the outer end 41 as shown in the figure generally comprises, in the periphery of the opening 41a, a hinge 401 and a pinch 402 that would protrude outwardly from the profile 400 in a plane view of the outer end 41. According to one or more embodiments, however, the lid 20 can be mounted on the lid-mounting part 15 while the container 40 comprising an opening 41a at the outer end 41 remains inserted into the hole 12, regardless of the direction. In order to achieve effects similar to those achieved by one or more embodiments, the housing 10 is not necessarily constituted in a manner such that the profile 400 of the outer portion 40a of the container 40 is enclosed in the inner periphery 150 of the lid-mounting part 15 while the container 40 remains inserted into and supported by the hole 12, regardless of the direction of the container 40 in the hole 12. For example, effects similar to those achieved by one or more embodiments can be achieved by constituting the housing 10 as described below. When the container 40 is inserted into and supported by the hole 12, a part of the profile 400 of the outer portion 40a of the container 40 is protruded from the inner periphery 150 of the lid-mounting part 15 depending on the direction of the container 40 in the hole 12, the lid 20 is mounted on the housing 10 through the lid-mounting part 15, the lid 20 comes into contact with the outer portion 40a of the container 40, and the container 40 is guided in a direction such that the entire profile 400 is enclosed in the inner periphery 150 of the lid-mounting part 15.

In FIG. 2, "S" drawn on the outer surface 14a of the hole-formed part 14 of the housing indicates the hole 12 into which the container 40 accommodating a sample liquid (a sample) as liquid L is inserted, and "B" indicates the hole 12 into which the container 40 accommodating a developing liquid (a buffer) as liquid L is inserted.

The test device 1 according to one or more embodiments also comprises undulated surfaces 102d formed on at least a part of the outer surface 102a of the side wall 102, which is the lateral surface of the housing 10. The undulated surfaces 102d are formed of continuous plurality of grooves 102e in the direction in which the bottom wall 101 and the upper wall 103 of the housing 10 face each other. Because the undulated surfaces 102d are provided on the outer surfaces 102a of the side wall 102, slip caused when a user operates the test device with fingers can be prevented. When a plurality of test devices 1 according to one or more embodiments are arranged in a manner such that the outer surfaces 102a of the side walls 102 of the housings 10 are in contact with each other, the undulated surfaces 102d can be engaged with each other. An undulated surface is an example of a concave-convex surface. In the test device 1 according to one or more embodiments, concave-convex surfaces with different configurations may be provided instead of the undulated surfaces 102d. A concave-convex surface is formed of a plurality of continuous grooves extending in one direction, and a flat surface may be formed between grooves adjacent to each other. Concerning the plurality of grooves on the concave-convex surface, a configuration of a cross section of a plane vertical to the extending direction is not particularly limited. An example of a surface having a cross section with a curved configuration is an undulated surface shown in the figure. But a configuration of the cross section may be a rectangle or U-shape.

According to the examples shown in FIG. 1A to FIG. 5C, the upper surface 17a of the fixing part 17 is flat, and the blade 13 is provided in a manner such that the lateral surfaces 132 and 133 are positioned to be vertical to the upper surface 17a of the fixing part 17. In order to accelerate liquid L to leak by enlarging the leakage port 43 of the container 40 formed by the blade 13, the structure in the vicinity of the blade 13 can be adequately regulated. Specific variation examples are as described below.

Figure 6A:
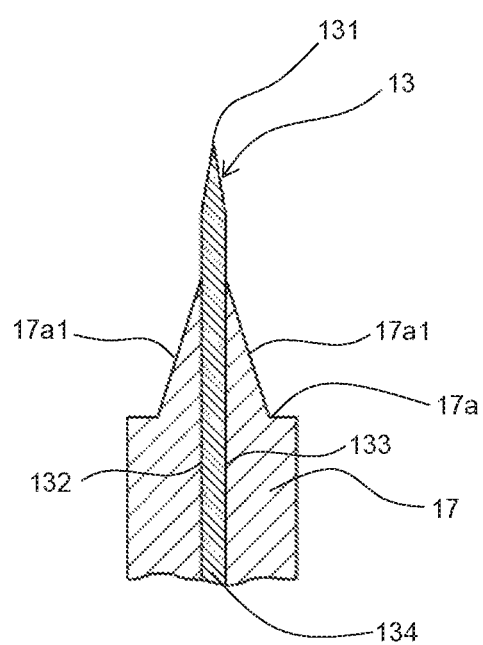
FIG. 6A schematically shows an end plane showing a variation example of a structure in the vicinity of a blade (a perforation/incision part) in the housing.
Figure 6B:
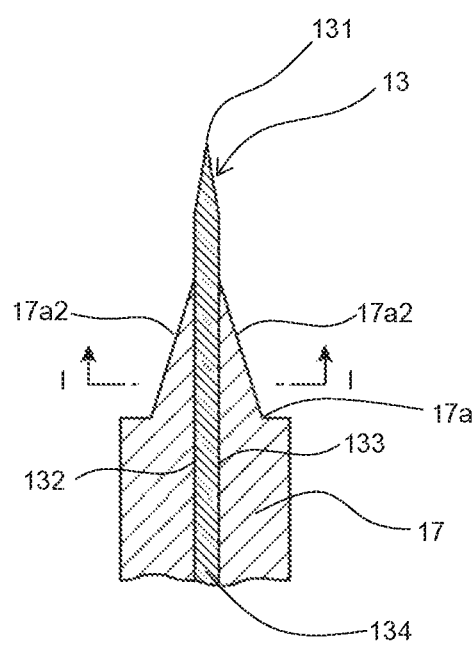
FIG. 6B schematically shows an end plane showing another variation example of a structure in the vicinity of a blade (a perforation/incision part) in the housing.
Figure 6C:
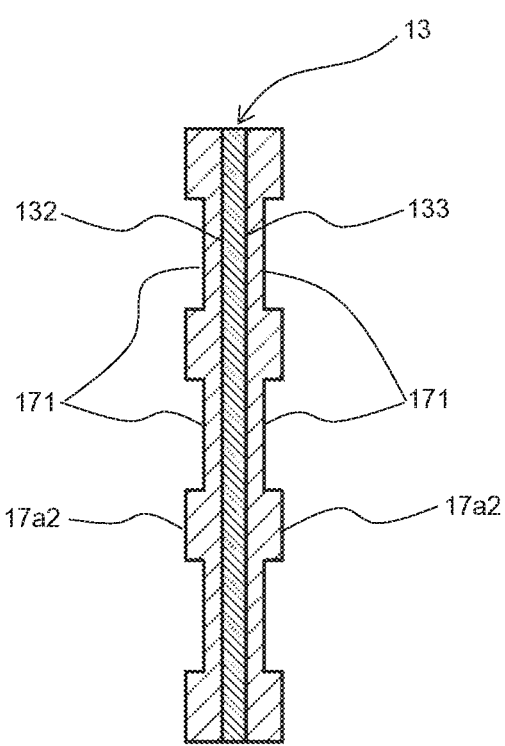
FIG. 6C shows an end plane of a variation example shown in FIG. 6B taken along the I-I line of the variation example shown in FIG. 6B.
Figure 6D:
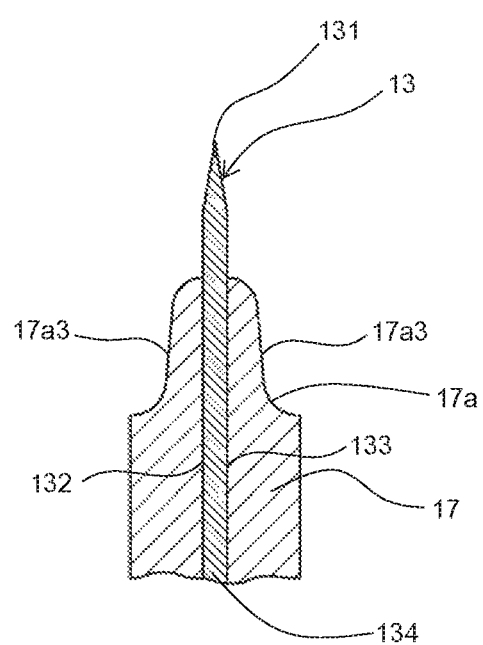
FIG. 6D schematically shows an end plane showing another variation example of a structure in the vicinity of a blade (a perforation/incision part) in the housing.

FIG. 6A, FIG. 6B, and FIG. 6D each schematically show a cross section taken at a plane vertical to the direction in which the edge 131 of the blade 3 extends in the vicinity of the fixing part 17 and the blade 13 of each variation example.

A variation example shown in FIG. 6A comprises the sloped portion 17a1 that is inclined to approach the edge 131, as the upper surface 17a of the fixing part 17 approaches the lateral surfaces 132 and 133 in the vicinity of the blade 13. With the constitution of this variation example, when the container 40 is pushed toward the base end 134 from the edge 131 of the blade 13, the leakage port 43 is incised not only by the blade 13 but also by the sloped portion 17a1 of the upper surface 17a of the fixing part 17. Thus, a larger leakage port 43 can be formed.

A variation example shown in FIG. 6B comprises the sloped portion 17a2 that is inclined to approach the edge 131, as the upper surface 17a of the fixing part 17 approaches the lateral surfaces 132 and 133 in the vicinity of the blade 13. As shown in FIG. 6C, the sloped portion 17a2 has a concave-convex structure comprising a plurality of concave grooves 171 extending along the direction from the fixing part 17 to the edge 131 of the blade 13 arranged in parallel at intervals. According to the constitution of this variation example, the container 40 is pushed from the edge 131 of the blade 13 toward the base end 134 of the blade 13, the leakage port 43 is incised not only by the blade 13 but also by the sloped portion 17a2 on the upper surface 17a of the fixing part 17, and liquid L efficiently leaks into the internal space 11 through a plurality of the concave grooves 171. Thus, such constitution may be preferable.

A variation example shown in FIG. 6D comprises the sloped portion 17a3 that is inclined to approach the edge 131, as the upper surface 17a of the fixing part 17 approaches the lateral surfaces 132 and 133 in the vicinity of the blade 13. A slope of the sloped portion 17a3 continuously becomes shallow as it approaches the lateral surfaces 132 and 133. According to the constitution of such variation example, the container 40 is pushed from the edge 131 of the blade 13 toward the base end 134 of the blade 13, and the leakage port 43 is incised not only by the blade 13 but also by the sloped portion 17a3 on the upper surface 17a of the fixing part 17. Thus, a larger leakage port 43 can be formed.

OTHER FEATURE 1 OF THE TEST DEVICE 1 ACCORDING TO THE FIRST EXAMPLE

The test device 1 according to the first example comprises:
a housing 10 for accommodating a chromatography support 30, the housing enclosing an internal space 11 where chromatography involving the use of the chromatography support 30 is carried out,
wherein the housing 10 comprises a supporting part for supporting two or more containers 40 accommodating liquids L used for chromatography, and
a perforation/incision part 13 that perforates or incises the two or more containers 40 supported by the supporting part to leak the liquids L from the containers 40 into the internal space 11.

This feature is referred to as the "other feature 1."

The supporting part may be a part of the housing in which a structure supporting two or more containers accommodating liquids for chromatography is formed. A specific example of the supporting part is the hole-formed part 14 of the housing provided with holes 12 through which two or more containers 40 are supported.

The test device 1 having the other feature 1 is capable of perforation or incision of two or more containers 40 at a single perforation/incision part 13 to leak liquids L from the containers 40 into the internal space 11. Compared with the test device equipped with two or more perforation/incision parts corresponding to two or more containers 40, accordingly, the test device 1 having the other feature 1 is simply structured, and such test device can be produced at a lower cost. In such a case, the test device 1 is not necessarily equipped with the lid 20. For example, the test device 1 that does not comprise the lid 20 but comprises the housing 10 may be used, and such test device 1 may be operated in a manner such that a user pushes the outer portions 40a of the containers 40 supported by the holes 12 of the hole-formed part 14 of the housing with fingers.

In the test device 1 having the other feature 1, preferably, the perforation/incision part may be the blade 13, and the supporting part is the hole-formed part 14 provided with two or more holes 12 through which two or more containers 40 are supported. Thus, two or more containers 40 are provided to face each other at different positions on the edge 131 of the single blade 13. The two or more holes 12 are constructed in a manner such that the containers 40 are guided by the blade 13 from the position facing the edge 131 of the blade 13 to the site to be incised by the blade 13 when the containers 40 inserted into the two or more holes 12 are pushed toward the blade 13.

In one or more embodiments, the test device 1 having the other feature 1 more preferably comprises some or all the features described with reference to the test device 1 according to the first example described herein.

OTHER FEATURE 2 OF THE TEST DEVICE 1 ACCORDING TO THE FIRST EXAMPLE

The test device 1 according to the first example comprises:
a chromatography support 30; and
a housing 10 accommodating the chromatography support 30, the housing enclosing an internal space 11 where chromatography involving the use of the chromatography support 30 is carried out,
wherein the housing 10 comprises:
a bottom wall 101;
an upper wall 103 facing the bottom wall 101;
a side wall 102 connecting the periphery of the bottom wall 101 to the periphery of the upper wall 103; and
a support-mounting part 16 for providing the chromatography support 30 in a direction facing the upper wall 103 in a position closer to the upper wall 103 between the bottom wall 101 and the upper wall 103 in the direction in which the bottom wall 101 faces the upper wall 103,
the chromatography support 30 is provided on the support-mounting part 16 of the housing 10, and
a part 103c of the upper wall 103 facing the chromatography support 30 is visible light permeable.

This feature is referred to as the "other feature 2."

In the test device 1 having the other feature 2, the chromatography support 30 (hereafter, it is occasionally referred to as the "support 30") is positioned to face the upper wall 103 of the housing 10 in a position close to the upper wall 103, and a part 103c of the upper wall 103 is visible light permeable. Accordingly, the support 30 is sufficiently visible at the time of chromatographic development.

The part 103c of the upper wall 103 of the housing 10 is not particularly limited, provided that it is visible light permeable to the extent that the support 30 in the housing 10 is visually observable from the outside of the housing 10 through the part 103c of the upper wall 103 under application of light including visible light, such as sunlight.

As shown in, for example, FIG. 1A and FIG. 4A, a specific configuration of the support-mounting part 16 is a protrusive part rising upright from the bottom wall 101 toward the upper wall 103 in the internal space 11, which is provided with an upper surface 16a on which at least a part of the support 30 can be provided.

The whole of the support 30 is not necessary provided on the support-mounting part 16, and it may be provided in at least a part thereof. At least a part comprising the detection part 32 of the support 30 may be preferably provided on the support-mounting part 16, so that the detection part 32 is visible through the upper wall 103.

In the test device 1 having the other feature 2, the housing 10 comprises the side wall 102. When the test device 1 is disposed on a horizontal surface to adjust the bottom wall 101 of the housing 10 to be on the lower side, accordingly, the test device can be easily operated while touching the side wall 102 of the housing 10 with fingers; that is, the test device is easy to handle. While a height of the side wall 102 can be adequately determined, it may be preferably 4 mm or more, and more preferably 6 mm to 20 mm. By providing the support 30 on the support-mounting part 16 of the housing 10, the support 30 is provided in a position closer to the upper wall 103 even if the housing 10 has a thickness in accordance with the height of the side wall 102. Thus, visual observation is easily carried out through the upper wall 103. When the test device 1 having the other feature 2 is disposed on a horizontal surface to adjust the bottom wall 101 of the housing 10 to be on the lower side, a portion disposed on the support-mounting part 16 of the support 30 is positioned in a position higher than the bottom wall 101. Thus, the portion disposed on the support-mounting part 16 of support 30 is less likely to come into direct contact with liquid L leaked from the containers 40 at the perforation/incision part 13, and chromatographic development can be easily performed with high accuracy.

The test device 1 having the other feature 2 does not necessarily comprise the lid 20.

In one or more embodiments, the test device 1 having the other feature 2 more preferably comprises some or all the features described with reference to the test device 1 according to the first example described herein.

In the test device 1 having the other feature 2, the distance D2 between a part of the support 30 provided on the support-mounting part 16 and the upper wall 103 may be preferably 10 mm or less (see FIG. 4A, FIG. 4B, and FIG. 14). The term "the distance D2 between a part of the support 30 provided on the support-mounting part 16 and the upper wall 103" used herein refers to the shortest distance among various distances between the part of the support 30 provided on the support-mounting part 16 and the upper wall 103. The distance D2 between the entire part of the support 30 provided on the support-mounting part 16 and the upper wall 103 may be preferably 10 mm or less. When the distance D2 is 10 mm or less, the part of the support 30 provided on the support-mounting part 16 is in a position sufficiently close to the upper wall 103. Under visible light, accordingly, visual observation can be easily performed from the outside of the housing 10 through the upper wall 103.

Figure 11:
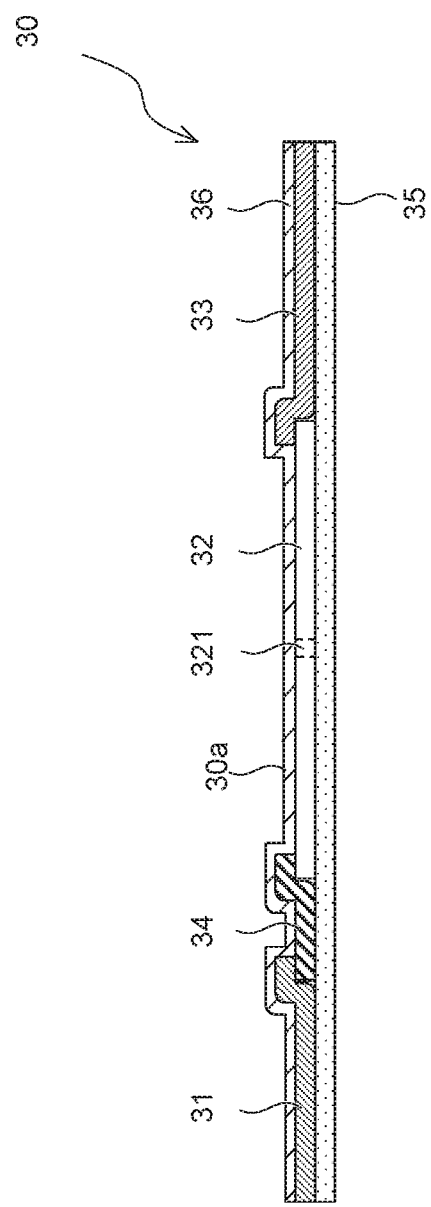
FIG. 11 shows an example in which the surface 30a facing the upper wall 103 of the chromatography support 30 shown in FIG. 9 is covered with the protective film 36.
Figure 12:
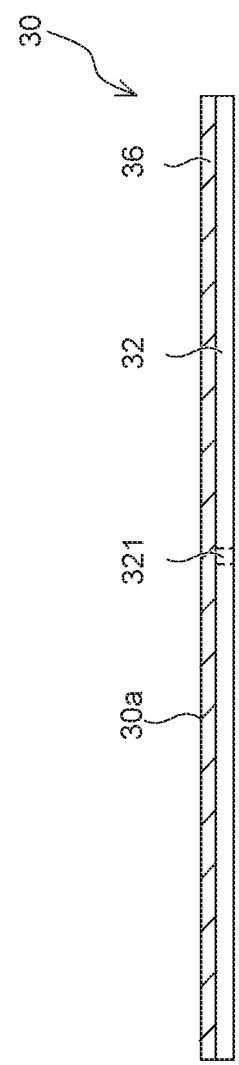
FIG. 12 shows an example in which the surface 30a facing the upper wall 103 of the chromatography support 30 shown in FIG. 10 is covered with the protective film 36.

In the test device 1 having the other feature 2, a surface 30a of the support 30 facing the upper wall 103 may be preferably covered by the visible light permeable protective film 36, as shown in FIG. 11 and FIG. 12. FIG. 11 shows an example of the chromatography support 30 shown in FIG. 9 comprising the surface 30a facing the upper wall 103 covered by the protective film 36. FIG. 12 shows an example of the chromatography support 30 shown in FIG. 10 comprising the surface 30a facing the upper wall 103 covered by the protective film 36. Use of the support 30 comprising the surface 30a covered by the visible light permeable protective film 36 may be preferable since chromatographic development is less likely to be influenced by the contact between the surface 30a of the support 30 and the upper wall 103. This example is particularly effective when the distance D2 is as short as 10 mm or less. The visible light permeable protective film 36 can be a visible light permeable film through which liquid L does not substantially penetrate. The protective film 36 is not particularly limited, provided that it is visible light permeable to the extent that the lower surface of the protective film 36 of the support 30 is visually observable with the application of light including visible light, such as sunlight.

In one or more embodiments of the test device 1 having the other feature 2, preferably, the part 103c of the upper wall 103 of the housing 10 facing the support 30 has a thickness of 20 μm to 10 mm and total luminous transmittance of 70% or more. The total luminous transmittance represents the ratio of the transmitted luminous flux to the parallel incident luminous flux of the test piece, which is standardized under JIS 7375:2008. In such a case, visual observation of the support 30 can be performed particularly clearly from the outside of the housing 10 through the part 103c of the upper wall 103.

Figure 13:
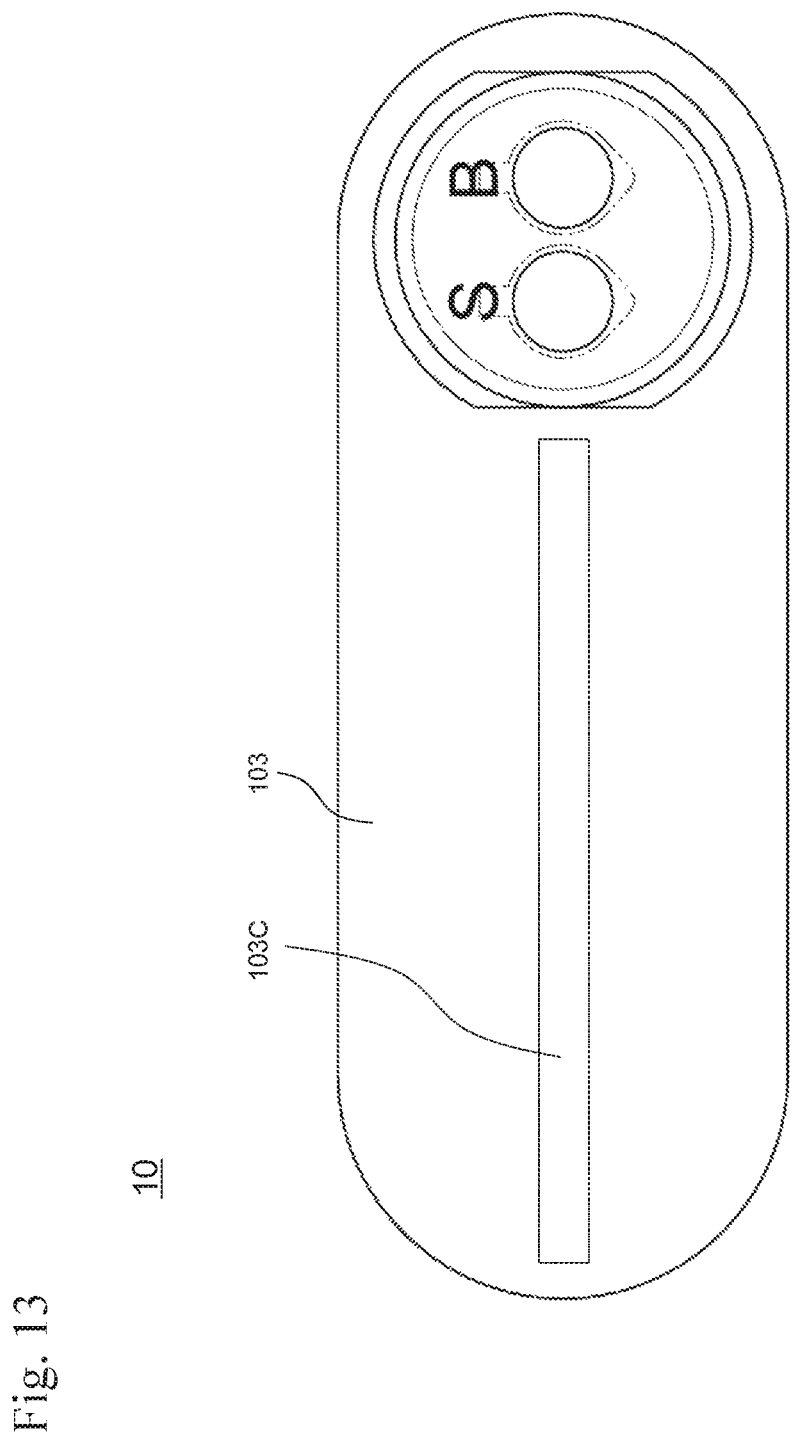
FIG. 13 shows a plane view of the housing of the test device according to one or more embodiments of the present invention.

In the test device 1 having the other feature 2, in the plane view of the housing 10, an area accounting for 5% or more of the total area of the housing 10 may be preferably a visible light permeable part 103c of the upper wall 103 facing the support. FIG. 13 shows a plane view of the housing 10. The visible light permeable part 103c of the upper wall 103 facing the support may be preferably 5% or more relative to the total area of the housing 10 when the housing 10 is viewed horizontally, as shown in the plane view shown in FIG. 13. This example may be preferable since visibility of the support 30 from the outside of the housing 10 through the part 103c of the upper wall 103 is particularly high.

In one or more embodiments of the test device 1 having the other feature 2, preferably, at least either one of the outer surface (the upper surface) 103a and the inner surface (the lower surface) 103b of the upper wall 103 of the housing 10 is provided with an antireflection member 140. The term "the outer surface" of the upper wall refers to a surface of the upper wall outside the housing, and the term "inner surface" of the upper wall refers to a surface of the upper wall inside the housing. FIG. 14 shows a partial structure associated with the housing 10 of the test device 1 according to this example in which the antireflection member 140 is provided on an outer surface (an upper surface) 103a of the upper wall 103 of the housing 10. By providing the antireflection member 140 on the upper wall 103 of the housing 10, visual observation of the support 30 can be performed particularly clearly from the outside of the housing 10 through the part 103c. The total luminous transmittance of the antireflection member 140 may be preferably 2% or less, and more preferably 1% or less. The total luminous transmittance represents the ratio of the transmitted luminous flux to the parallel incident luminous flux of the test piece, which is standardized under JIS 7375:2008.

Figure 15B:
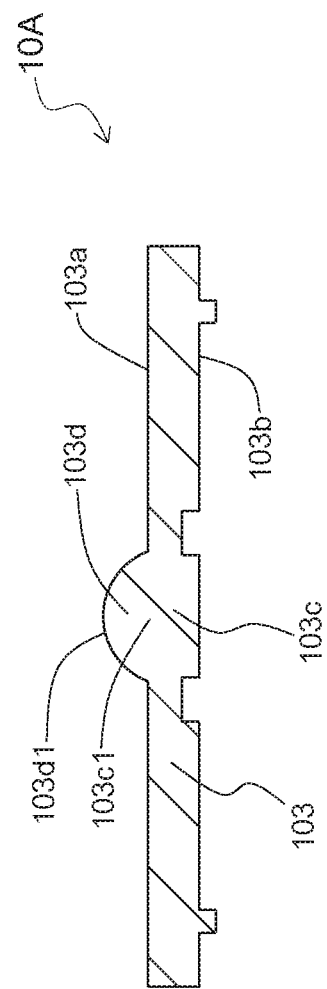
FIG. 15B shows an end plane of the upper housing member 10A shown in FIG. 15A taken along the I-I line.
Figure 16A:
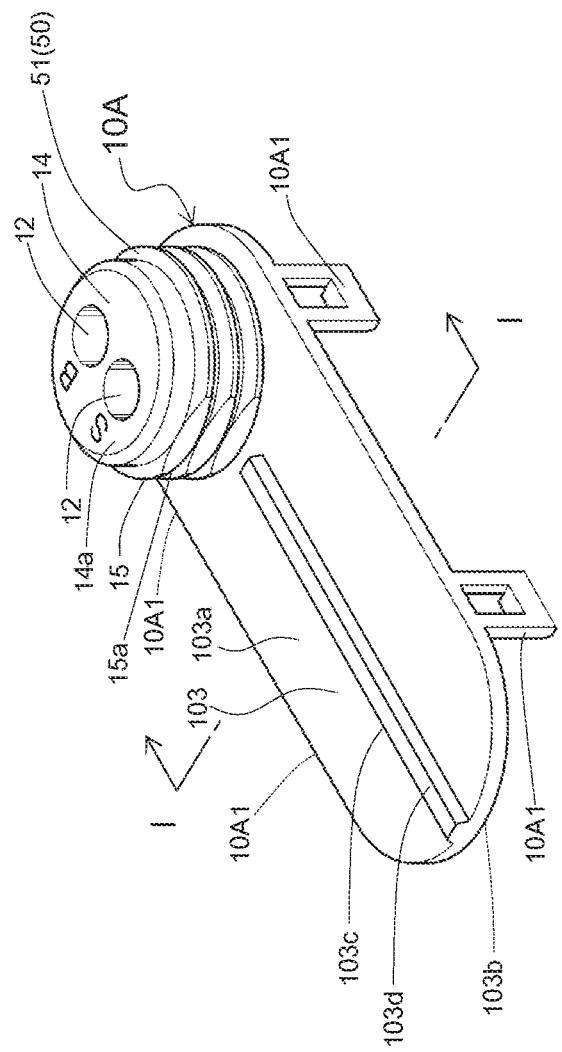
FIG. 16A shows a perspective view of the upper housing member 10A constituting the second example of the housing 10 of the test device 1 provided with the visible light permeable protrusive part 103d outside of the upper wall 103c.
Figure 16B:
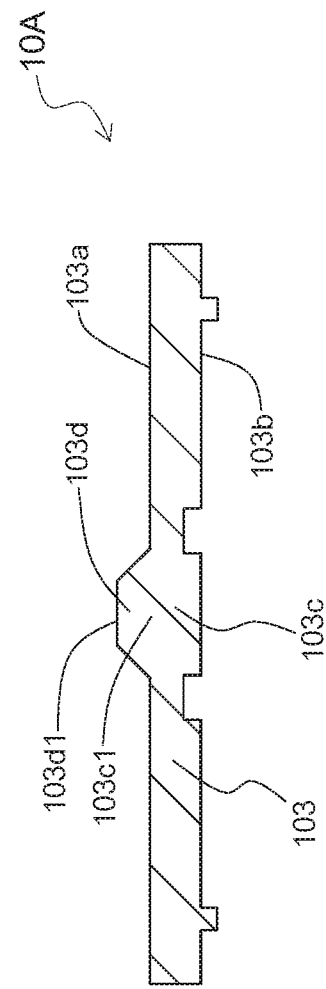
FIG. 16B shows an end plane of the upper housing member 10A shown in FIG. 16A taken along the I-I line.

In one or more embodiments, the test device 1 having the other feature 2 preferably comprises a visible light permeable protrusive part 103d extending along the support 30 toward the outside of the housing 10 in a position 103c1 outside of the housing 10 where the part 103c of the upper wall 103 of the housing 10 faces the support 30. FIG. 15A and FIG. 15B each show the upper housing member 10A constituting the first example of the housing 10 of the test device 1 according to one or more embodiments. FIG. 16A and FIG. 16B each show the upper housing member 10A constituting the second example of the housing 10 of the test device 1 according to one or more embodiments. The upper housing member 10A shown in FIG. 15A and FIG. 15B constitutes the first example of the housing 10 in combination with the lower housing member 10B shown in FIG. 1A. The upper housing member 10A shown in FIG. 16A and FIG. 16B constitutes the second example of the housing 10 in combination with the lower housing member 10B shown in FIG. 1A. In the first example of the housing 10, as shown in FIG. 15A and FIG. 15B, the outer surface 103*d*1 of the protrusive part 103*d* is a part of a cylindric surface around the axis along the direction of the protrusive part 103*d* extending along the support 30. In the second example of the housing 10, as shown in FIG. 16A and FIG. 16B, the outer surface 103*d*1 of the protrusive part 103*d* is a part of a polygonal tube surface around the axis along the direction of the protrusive part 103*d* extending along the support 30. With the use of the test device 1 comprising the housing 10 having the upper wall 103 with the protrusive part 103*d* formed thereon and having the other feature 2, an image of the support 30 is enlarged by the protrusive part 103*d* when the support 30 is observed under a visible light through the protrusive part 103*d* and the part 103*c* of the upper wall 103 of the housing 10. Thus, visibility of the support 30 can further be enhanced.

The protrusive part 103*d* of the upper wall 103 of the housing 10 is not particularly limited, provided that it is visible light permeable to the extent that the support 30 in the housing 10 is visually observable from the outside of the housing 10 through the protrusive part 103*d* and the part 103*c* of the upper wall 103 under application of light including visible light, such as sunlight.

OTHER FEATURE 3 OF THE TEST DEVICE 1 ACCORDING TO THE FIRST EXAMPLE

The test device 1 according to the first example also comprises:

a chromatography support 30 (a support 30); and a housing 10 accommodating the chromatography support 30, the housing enclosing an internal space 11 where chromatography involving the use of the support 30 is carried out, wherein the housing 10 comprises:

a supporting part for supporting containers 40 accommodating liquids L used for chromatography; and a perforation/incision part 13 that perforates or incises the containers 40 supported by the supporting part to leak the liquids L from the containers 40 into the internal space 11, the support 30 is accommodated in the housing 10 in a manner such that a part of the support 30 is positioned between the supporting part and the perforation/incision part 13, and the supporting part comprises a container guide that guides the containers 40 from position A where the containers 40 face the perforation/incision part 130 through the part of the support 30 to position B where the containers 40 are perforated or incised together with the part of the support 30 at the perforation/incision part 13 with the containers 40 being supported thereby.

This feature is referred to as the "other feature 3."

The supporting part may be a part of the housing in which a structure supporting the container accommodating a liquid for chromatography is formed. A specific example of the supporting part is the hole-formed part 14 of the housing provided with holes 12 through which the containers 40 are inserted and supported.

Examples of the container guide include holes 12 formed in the hole-formed part 14 of the housing. Each of the holes 12 functions as a guide hole that guides the container 40, which is inserted into and supported by the hole, from position A to position B.

A part of the support 30 positioned between the supporting part and the perforation/incision part 13 is the liquid receiver 31 of the support 30 according to an example shown in the figure. However, the part of the support 30 positioned between the supporting part and the perforation/incision part 13 is not limited thereto, and it may be a part other than the detection part 32 of the support 30 (e.g., an upstream end of development on the support 30).

FIG. 4A and FIG. 5A each schematically show a cross sectional view of the test device 1 in which the container 40 is located in position A. As shown in FIG. 4A and FIG. 5A, the container 40 located in position A is inserted into and supported by a hole (i.e., a container guide) 12 formed in the hole-formed part (the supporting part) 14 of the housing, it faces the edge 131 of the perforation/incision part 13 at the inner end 42, and a liquid receiver 31, which is a part of the support 30, is positioned between the inner end 42 of the container 40 and the edge 131 of the perforation/incision part 13.

FIG. 4B and FIG. 5C each schematically show a cross sectional view of the test device 1 in which the container 40 is located in position B. As shown in FIG. 4B and FIG. 5C, the container 40 located in position B is perforated or incised together with the liquid receiver 31, which is a part of the support 30, at the perforation/incision part 13.

The outer portion 40*a* of the container 40 in position A is located outside the housing 10. When the outer portion 40*a* of the container 40 is pushed into the housing 10, the container 40 is guided by the hole (i.e., the container guide) 12 to position B. While migrating from position A to position B, the inner end 42 of the container 40 and the liquid receiver 31 of the support 30 are pushed against the edge 131 of the perforation/incision part 13 and then perforated or incised. In such a case, liquid L leaked from the container 40 is able to come into contact with the liquid receiver 31 of the support 30 and penetrate into the liquid receiver 31 immediately with certainty. The test device 1 having the other feature 3 may be preferable since it is capable of efficiently bringing liquid L leaked from the container 40 into contact with the support 30.

The test device 1 having the other feature 3 is not necessarily equipped with the lid 20 shown in FIG. 1A to FIG. 5C. For example, the test device 1 that does not comprise the lid 20 but comprises the housing 10 may be used, and such test device 1 may be operated in a manner such that a user pushes the outer portion 40*a* of the container 40 supported by the hole 12 of the hole-formed part 14 of the housing with fingers.

In one or more embodiments, the test device 1 having the other feature 3 more preferably comprises some or all the features described with reference to the test device 1 according to the first example described herein.

SECOND AND THIRD EXAMPLES

The second example (FIG. 7) and the third example (FIG. 8) according to one or more embodiments of the present invention are described below. The constitutions and the functions in common with those according to the first example are numbered in the same manner and descriptions thereof are omitted.

In the test device 1 according to the first example, the chromatography support 30 is provided in the internal space 11 in a manner such that the direction X in which the hole-formed part 14 of the housing 10 faces the lid 20 and the container 40 is pushed toward the perforation/incision part 13 becomes orthogonal to the direction Y in which the portion comprising the detection part 32 of the chromatography support 30 provided in the internal space 11 of the housing 10 extends and liquid L develops. The test device 1 according to the first example comprising the chromatography support 30 provided in the internal space 11 is disposed on a horizontal surface, so that the container 40 is pushed downward in a vertical direction and liquid L is developed in a horizontal direction in the detection part 32 on the chromatography support 30.

However, the chromatography support 30 may be provided in any direction in the internal space 11 of the housing 10.

In the test device 1 according to the second example, the cross section of which is schematically shown in FIG. 7, for example, the chromatography support 30 is provided in the internal space 11 in a manner such that the direction X in which the hole-formed part 14 of the housing 10 faces the lid 20 and the container 40 is pushed toward the perforation/incision part 13 becomes approximately the same as the direction Y in which an area of the chromatography support 30 comprising the detection part 32 provided in the internal space 11 of the housing 10 extends and liquid L develops. The test device 1 according to the second example shown in FIG. 7 is used in a manner such that it is disposed on a horizontal surface, the container 40 is pushed downward in a vertical direction, and liquid L is developed upward in a vertical direction in the detection part 32 on the chromatography support 30. According to the second example, the chromatography support 30 is provided in the internal space 11 in a manner such that it is bent between the liquid receiver 31 and the detection part 32 and an area of the chromatography support 30 comprising the liquid receiver 31 is positioned between the hole-formed part 14 of the housing and the perforation/incision part 13.

In the test device 1 according to the third example, the cross section of which is schematically shown in FIG. 8, the chromatography support 30 is provided in the internal space 11 in a manner such that the direction X in which the hole-formed part 14 of the housing 10 faces the lid 20 and the container 40 is pushed toward the perforation/incision part 13 becomes approximately the same as the direction Y in which an area of the chromatography support 30 comprising the detection part 32 provided in the internal space 11 of the housing 10 extends and liquid L develops. The test device 1 according to the third example shown in FIG. 8 is used in a manner such that it is disposed on a horizontal surface, the container 40 is pushed in a horizontal direction, and liquid L is developed in a horizontal direction in the detection part 32 on the chromatography support 30. According to the third example, the chromatography support 30 is provided in the internal space 11 in a manner such that it is bent between the liquid receiver 31 and the detection part 32 and an area of the chromatography support 30 comprising the liquid receiver 31 is positioned between the hole-formed part 14 of the housing and the perforation/incision part 13.

According to one or more embodiments, although it is not shown, a test device is constructed in a manner such that a plurality of chromatography supports are provided in a single housing and a liquid leaked from the container comes into contact with a relevant chromatography support.

DESCRIPTION OF NUMERAL REFERENCES

1: Test device
10: Housing
102*a*: Outer surface (lateral surface) of the side wall of the housing
11: Internal space
12: Hole (container guide)
13: Perforation/incision site (blade)
14: Hole-formed part (supporting part) of the housing
15: Lid-mounting part
16: Support-mounting part
150: Inner periphery of the lid-mounting part
190: Elastic member
191 and 192: Elastic supporting pieces
20: Lid
21: Main lid part (a part of the lid facing the hole-formed part of the housing)
30: Chromatography support
40: Container
400: Profile of the outer portion of the container
50: Guide (lid guide)
51: Housing-side screw-engagement part
52: Lid-side screw-engagement part
102*d*: Undulated surface
L: Liquid
D: Distance between the hole-formed part of the housing and the part of the lid facing the hole-formed part of the housing All publications, patents, and patent applications cited herein are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A test device comprising an outer housing and a lid mounted on the outer housing, wherein the outer housing comprises:
    at least one hole;
    a hole-formed part where the at least one hole is formed;
    an internal space enclosed within the outer housing where chromatography using a chromatography support is carried out; and
    a perforation/incision part provided in the internal space,
    wherein the internal space is communicated with the outside of the outer housing through the at least one hole, allowing at least one container accommodating a liquid used for chromatography to be inserted and supported,
    wherein the perforation/incision part is configured to perforate or incise the container, in order to leak the liquid from the container into the internal space,
    wherein at least either one of the outer housing or the lid comprises a guide configured to guide the lid to the outer housing in a manner such that the lid can migrate from a first position to a second position while covering the hole-formed part of the outer housing with the lid and supporting the container through the at least one hole,
    wherein the first position is a position where the lid covers the hole-formed part and an outer portion of the container protruded toward the lid through the at least one hole and the container is not perforated or incised at the perforation/incision part, wherein a distance between the hole-formed part and a part of the lid facing the hole-formed part at the first position is larger than the distance at the second position, and wherein, while the lid is allowed to migrate from the first position to the second position, the outer housing and the lid are configured to be guided by the guide in a manner such that the part of the lid abuts against an end of the outer portion of the container, the container is configured to be pushed toward the perforation/incision part, and the container is perforated or incised at the perforation/incision part to leak the liquid into the internal space.

2. The test device according to claim 1, wherein the outer housing further comprises a lid-mounting part surrounding the hole-formed part of the outer housing, wherein, when the outer housing with the container inserted into and supported by the at least one hole of the outer housing is viewed from the outside of the outer housing in a through-hole direction, the outer housing is constructed in a manner such that a profile of the outer portion of the container is enclosed within the inner periphery of the lid-mounting part.

3. The test device according to claim 1, wherein the guide comprises a power boost mechanism that allows the lid mounted on the outer housing to migrate from the first position to the second position.

4. The test device according to claim 3, wherein the guide comprises screw-engagement parts formed on the lid and the outer housing, and the screw-engagement parts are engaged with each other in a manner such that, when the lid mounted on the outer housing in the first position is revolved around an axis along a direction in which the hole-formed part of the outer housing faces the lid, the lid migrates along the axis toward the hole-formed part of the outer housing.

5. The test device according to claim 1, wherein the outer housing further comprises, in a position surrounding the at least one hole, an elastic member that urges the container supported by the at least one hole against an axis of the hole and retains the position of the container within the hole.

6. The test device according to claim 1, wherein a lateral surface of the outer housing comprises a concave-convex surface.

* * * * *